United States Patent
Igarashi

(10) Patent No.: US 8,406,847 B2
(45) Date of Patent: Mar. 26, 2013

(54) BIOLOGICAL OBSERVATION APPARATUS AND METHOD

(75) Inventor: Makoto Igarashi, Hachioji (JP)

(73) Assignee: Olympus Medical Systems Corporation, Tokyo (JP)

( * ) Notice: Subject to any disclaimer, the term of this patent is extended or adjusted under 35 U.S.C. 154(b) by 299 days.

(21) Appl. No.: 12/483,684

(22) Filed: Jun. 12, 2009

(65) Prior Publication Data

US 2009/0312628 A1 Dec. 17, 2009

(30) Foreign Application Priority Data

Jun. 12, 2008 (JP) ................. 2008-154432

(51) Int. Cl.
*A61B 5/05* (2006.01)
(52) U.S. Cl. ......... 600/407; 600/310; 600/473; 600/476
(58) Field of Classification Search .......... 600/425, 600/427, 437, 473, 476, 310, 323, 328, 407; 382/128, 130, 140

See application file for complete search history.

(56) References Cited

U.S. PATENT DOCUMENTS

| | | | | |
|---|---|---|---|---|
| 6,754,518 | B1 * | 6/2004 | Lloyd et al. | 600/407 |
| 7,144,370 | B2 * | 12/2006 | Fomitchov | 600/438 |
| 7,251,518 | B2 * | 7/2007 | Herrmann | 600/322 |
| 2004/0127782 | A1 | 7/2004 | Sfez et al. | |
| 2005/0085725 | A1 * | 4/2005 | Nagar et al. | 600/437 |
| 2005/0256403 | A1 | 11/2005 | Fomitchov | |

FOREIGN PATENT DOCUMENTS

| | | |
|---|---|---|
| JP | 9-318603 | 12/1997 |
| JP | 2000-88743 | 3/2000 |
| JP | 2006-204431 | 8/2006 |

OTHER PUBLICATIONS

Extended European Search Report dated Nov. 25, 2009.

* cited by examiner

*Primary Examiner* — James Kish
*Assistant Examiner* — Michael N Fisher
(74) *Attorney, Agent, or Firm* — Scully, Scott, Murphy & Presser, P.C.

(57) ABSTRACT

A biological observation apparatus according to an aspect of the present invention includes a sound wave radiating unit that radiates a sound wave into an object to be examined, a light radiating unit that radiates first light having a predetermined wavelength and second light different from the first light into a portion of the object influenced by the sound wave, a detector that detects reflected light of the first light and reflected light of the second light, and a calculation unit that calculates characteristic information of the object based on the reflected light of the first light and the reflected light of the second light.

14 Claims, 15 Drawing Sheets

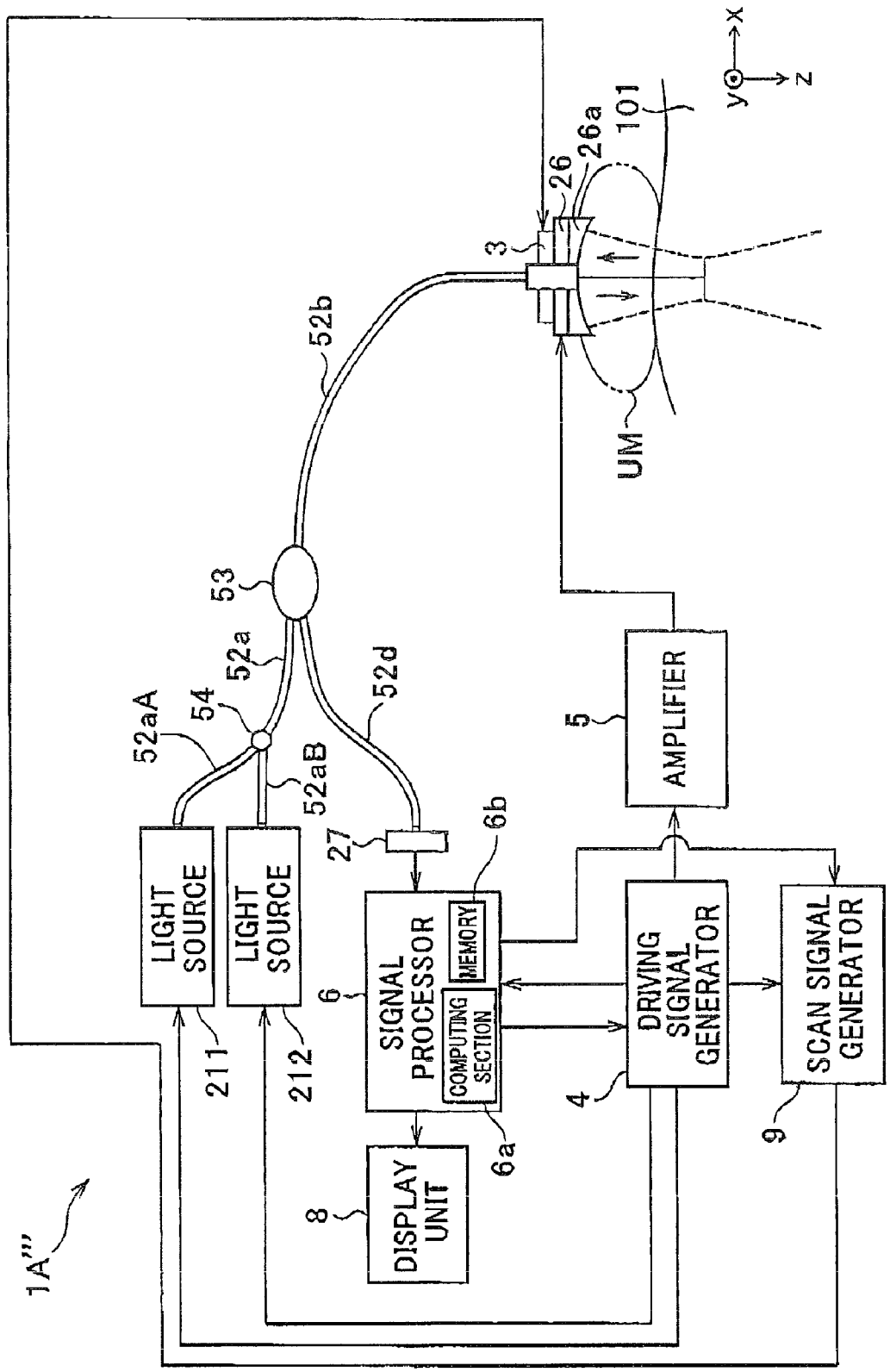

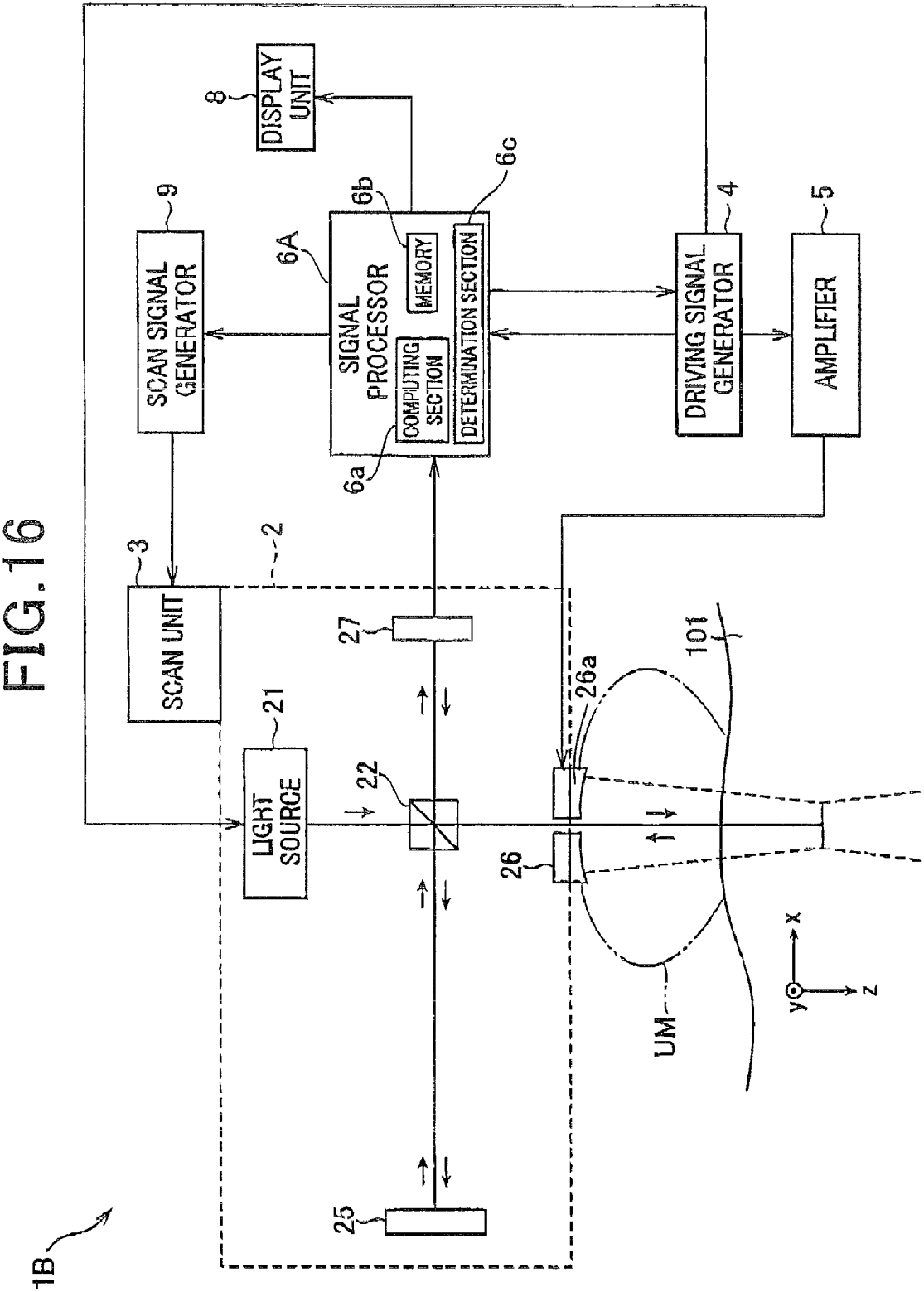

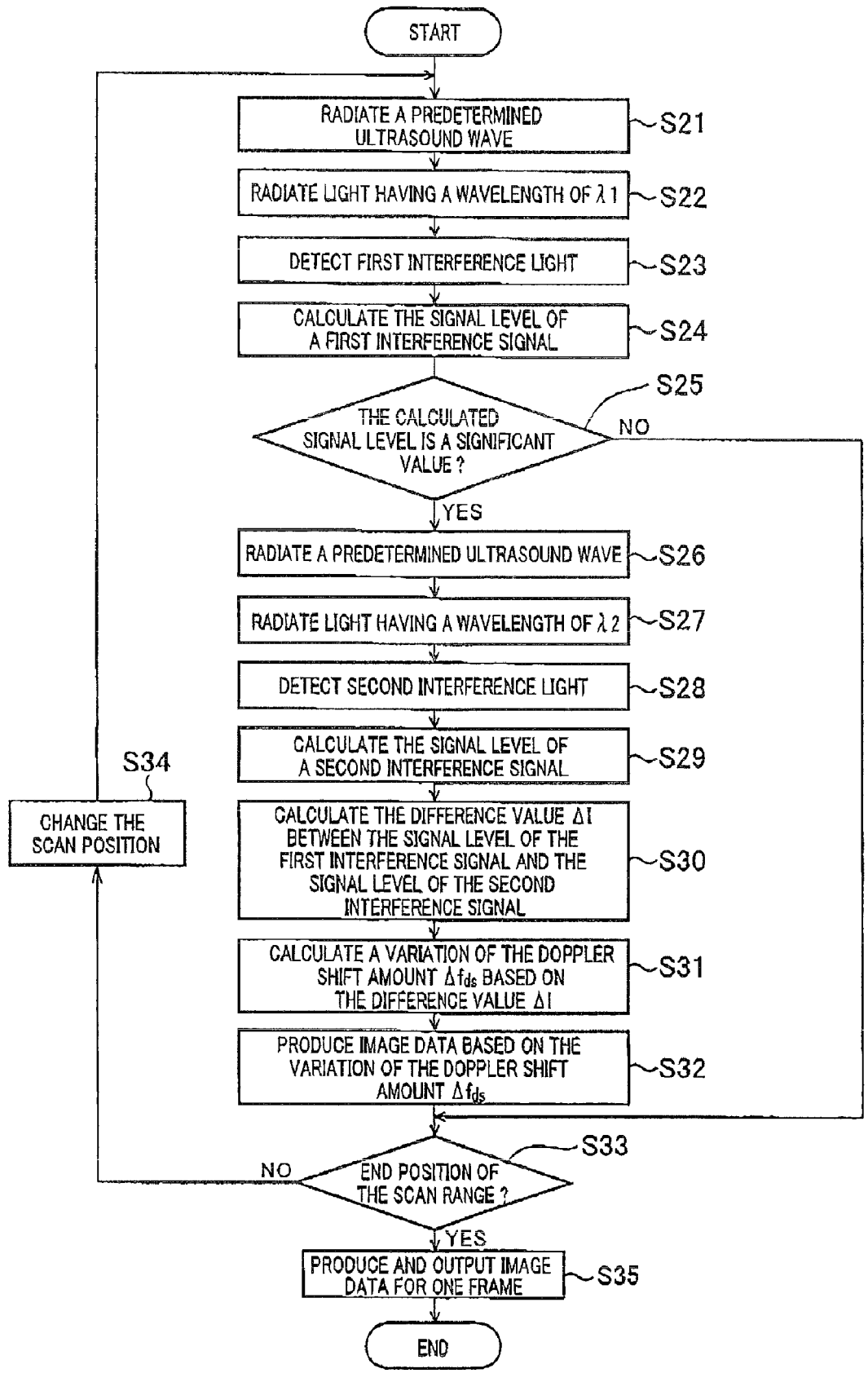

BIOLOGICAL OBSERVATION APPARATUS AND METHOD

CROSS REFERENCE TO RELATED APPLICATION

The present application relates to and incorporates by reference Japanese Patent application No. 2008-154432 filed on Jun. 12, 2008.

BACKGROUND OF THE INVENTION

1. The Field of the Invention

The present invention relates to a biological observation apparatus and a method and, more particularly, to a biological observation apparatus and a method which use a sound wave and light to obtain characteristic information indicative of internal states of an object to be examined.

2. Related Art

In recent years, as optical tomographic imaging for a living body, there have been known optical CT (computed tomography), optical coherence tomography (hereinafter, referred to as "OCT"), and photoacoustic tomography.

The optical CT utilizes near-infrared light of a wavelength ranging from 700 nm to 1200 nm, which is comparatively weakly influenced by scattering in a living body. Therefore, the optical CT enables obtaining tomograms of deep parts in the living body, such as up to several centimeters under a mucous membrane.

OCT, which utilizes interference, can obtain tomographic images of a living body up to a depth of about 2 mm with high resolution (several μm to several tens of μm) in a short time. The OCT has already been put into practice in diagnosing retinopathy in the ophthalmic field. Therefore, the OCT has attracted very keen interest in the medical world.

Although the optical CT can obtain information on a deep part of a living body, its spatial resolution is as low as several millimeters. In contrast, it is difficult for the OCT to perform observation at a depth of about 2 mm or more under a mucous membrane and to provide a good quality image of tumor tissue, such as a cancer. This is because the optical coherence is greatly disturbed by the influence of absorption of light by blood or strong scattering in the deep parts of a living body and tumor tissue.

Considering this situation, a technique for obtaining internal information from a living body other than using optical CT and OCT has been disclosed in Japanese Patent Laid-open Publication No. 2000-88743. In this technique, ultrasound waves and light having a single wavelength are radiated into a target portion inside a living body in order to detect how much the light is scattered by the ultrasound wave in the target portion. Thereby, information on the target portion of the living body can be obtained.

An optical measurement apparatus having the above-described configuration disclosed in Japanese Patent Laid-open Publication No. 2000-88743 obtains a value of how much the light is scattered. The value depends on indexes of refraction of a nucleus, cytoplasm and the like, which are substances existing in a living body. The publication states that each index of refraction of the substances constituting the living body is approximately 1.4.

The optical measurement apparatus uses light having a single wavelength to detect how much light is scattered. In consequence, due to the above-mentioned factors, the apparatus can obtain the information depending on how much the light is scattered only in a narrow dynamic range, thereby generating a tomographic image in which the difference of brightness between a bright section and a dark section is small.

As a result, for example, the optical measurement apparatus outputs a tomographic image in which the shape of tumor tissue is difficult to identify. Consequently, there is a problem that the operator is burdened during an observation of a target portion using the tomographic image.

SUMMARY OF THE INVENTION

The present invention has been made in consideration of the foregoing conventional situation, and an object of the present invention is to provide a biological observation apparatus and a method which reduce the burden on the operator when observing tumor tissue.

A biological observation apparatus according to an aspect of the present invention comprises a sound wave radiating unit that radiates a sound wave into an object to be examined; a light radiating unit that radiates first light having a predetermined wavelength and second light different from the first light into a portion of the object influenced by the sound wave; a detector that detects reflected light of the first light and reflected light of the second light; and a calculation it that calculates characteristic information of the object based on the reflected light of the first light and the reflected light of the second light.

BRIEF DESCRIPTION OF THE DRAWINGS

In the accompanying drawings:

FIG. 15 is a diagram showing a modification of the biological observation apparatus shown in FIG. 10;

FIG. 16 is a block diagram exemplifying an outline of a biological observation apparatus according to a second embodiment of the present invention; and FIG. 17 is a flowchart showing an example of a process performed in the biological observation apparatus shown in FIG. 16.

DETAILED DESCRIPTION OF THE PREFERRED EMBODIMENTS

Hereinafter, embodiments of the present invention will now be described in connection with the accompanying drawings.

Referring to FIGS. 1 to 6, a biological observation apparatus according to the first embodiment of the present invention will now be described.

Figure 1:
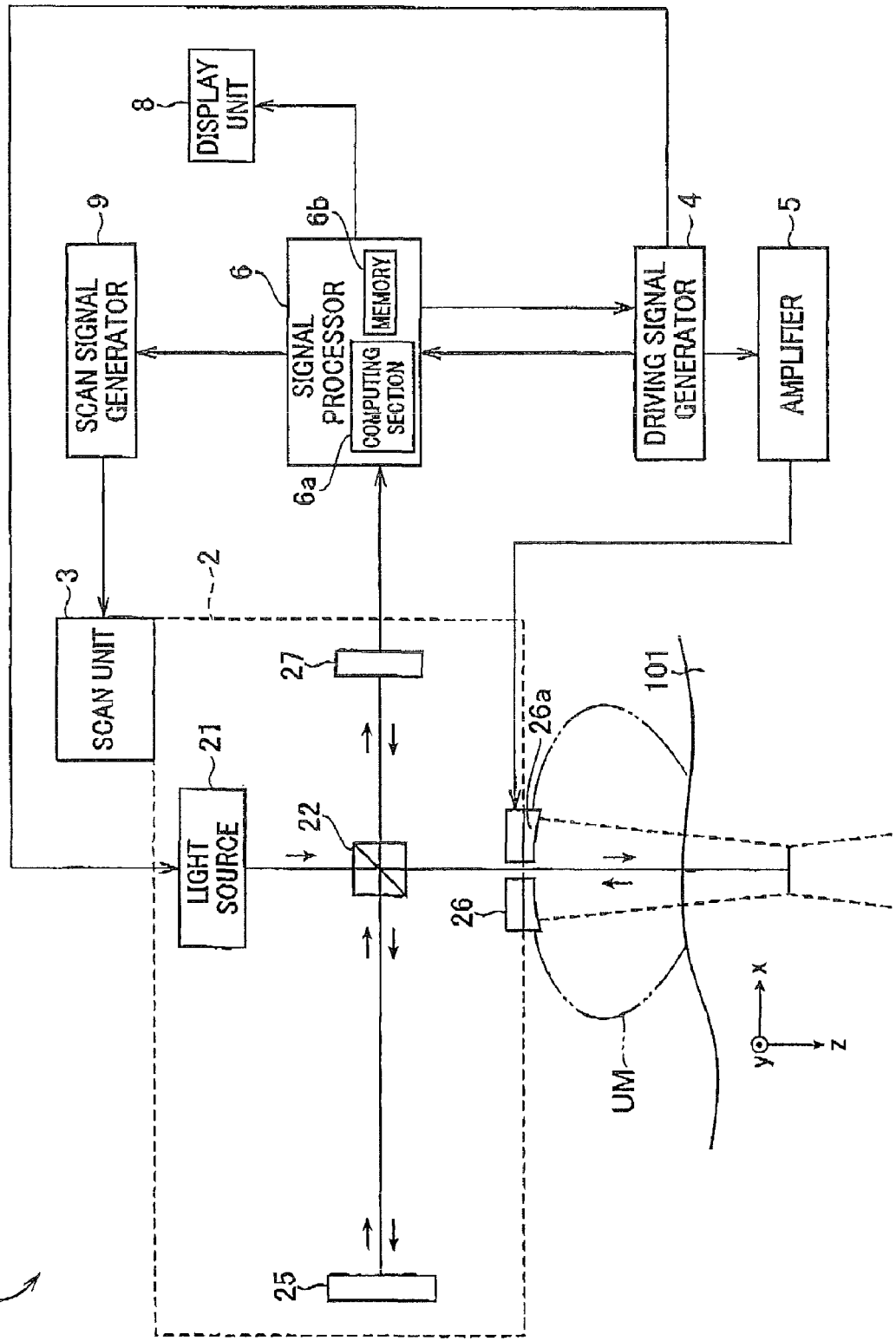
FIG. 1 is a block diagram exemplifying an outline of a biological observation apparatus according to a first embodiment of the present invention.

FIG. 1 outlines a biological observation apparatus 1. This biological observation apparatus 1 includes, as shown in FIG. 1, a radiation/reception unit 2, a scan unit 3, a driving signal generator 4, an amplifier 5, a signal processor 6, a display unit 8, and a scan signal generator 9, which are main parts.

The radiation/reception unit 2 radiates ultrasound waves (sound waves) and light into living tissue 101, which is an object to be examined, and can receive object light, which is the light from the radiation/reception unit 2 reflected and scattered from the living tissue 101. The scan unit 3 changes the position of the unit 2 (scan position) in response to a scan signal outputted from the scan signal generator 9 and makes the unit 2 radiate the ultrasound waves and light. The display unit 8 comprises a monitor.

The radiation/reception unit 2 has a light source 21, a half mirror 22, a reference mirror 25, an ultrasound transducer 26 and an acoustic lens 26a with openings formed at their center, and a light detector 27.

The light source 21 emits light having a wavelength of $\lambda 1$ and light having a wavelength of $\lambda 2$ alternately based on the timing at which the light source 21 receives a light source drive signal from the driving signal generator 4. The light having a wavelength of $\lambda 1$ and the light having a wavelength of $\lambda 2$ can reach the object portion to be examined in the living tissue 101. The light of wavelength $\lambda 1$ and the light of wavelength $\lambda 2$ have respective wavelengths such that absorbances (absorption characteristic) thereof with respect to the blood are approximately equal to each other. Specifically, the light source 21 is composed of, for example, a wavelength tunable laser source (not shown) or a combination of a white light source or a SLD (Super Luminescent Diode) and an interference filter (not shown).

Figure 2:
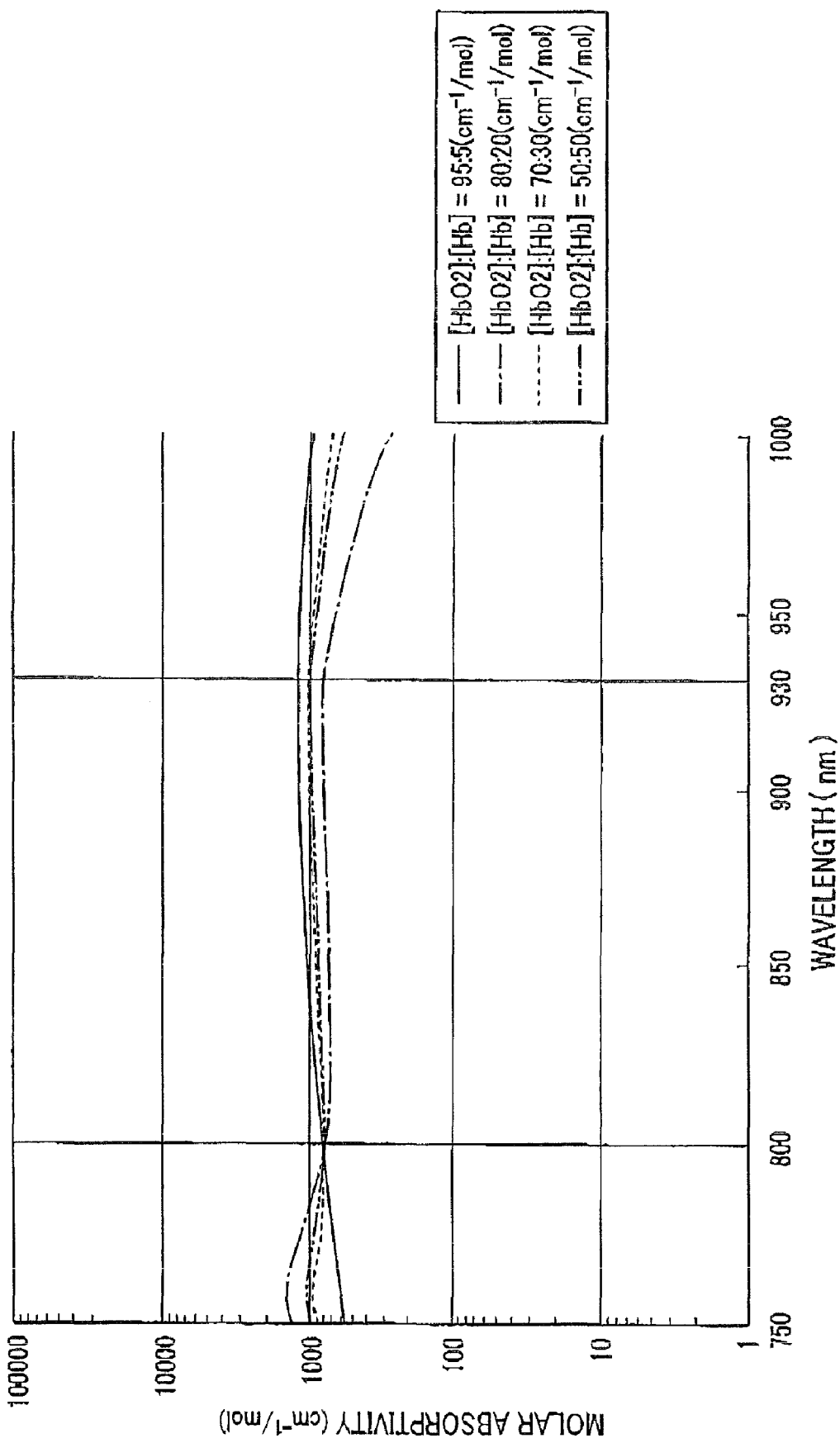
FIG. 2 is a diagram showing a wavelength dependency of absorbance corresponding to concentrations of oxygenated hemoglobin and hemoglobin in the blood.

The wavelength $\lambda 1$ and the wavelength $\lambda 2$ have values, which are different from each other ($\lambda 1 \neq \lambda 2$), within a range from 800 nm to 930 nm where sensitivity with respect to the change of oxygen saturation in the blood is low and absorbance (molar absorptivity) of the wavelength $\lambda 1$ and the wavelength $\lambda 2$ becomes approximately equal to each other. The light having a wavelength of $\lambda 1$ and the light having a wavelength of $\lambda 2$ are selected such that the absolute value of the difference between them (the value of $|\lambda 1 - \lambda 2|$) is as large as possible. In the present embodiment, it is preferable to select two wavelengths of 800 nm and 930 nm for $\lambda 1$ and $\lambda 2$. FIG. 2 shows an example of the wavelength dependency of absorbance (molar absorptivity) corresponding to concentrations of oxygenated hemoglobin ($HbO_2$) and hemoglobin (Hb) in the blood.

In addition, the light of wavelength $\lambda 1$ and the light of wavelength $\lambda 2$ may be pulsed waves, and not limited to continuous waves.

The light source 21 emits the light of wavelength $\lambda 1$ (or $\lambda 2$) to the half mirror 22 based on a light source drive signal provided from the driving signal generator 4.

Of the light which has traveled from the light source 21, the half mirror 22 reflects part of that light so that the reflected light is radiated toward the reference mirror 25 and allows the remaining part of that light to be transmitted toward the ultrasound transducer 26. The light which has traveled from the half mirror 22 to the reference mirror 25 is reflected by the reference mirror 25, and then made to enter the half mirror 22 as reference light. The light which has traveled from the half mirror 22 to the ultrasound transducer 26 passes through the opening formed at the center of the ultrasound transducer 26 and the acoustic lens 26a, before being radiated to the living tissue 101.

In the present embodiment, a space between (the acoustic lens 26a of) the radiation/reception unit 2 and the living tissue LT is filled with an ultrasound transmissive medium UM, which is, for example, water, before each unit of the biological observation apparatus 1 performs operations for obtaining biological information of the living tissue 101.

This ultrasound transducer 26 is driven in response to the ultrasound wave drive signal provided from the driving signal generator 4 and radiates a predetermined ultrasound wave, which is a continuous wave, toward the living tissue 101 along the axis of light passing through the opening. The ultrasound wave travels through the inside of the living tissue 101 as a cyclic compressional wave while the ultrasound wave is converged by the acoustic lens 26a. The ultrasound wave converges at a predetermined area located in the depth direction (Z-axis direction shown in FIG. 1) of the living tissue 101.

Note that the ultrasound wave radiated from the ultrasound transducer 26 is not limited to the continuous wave. For example, a pulse wave may be used.

The acoustic lens 26a of the present embodiment can appropriately change the area (position), at which the ultrasound wave converges, in the depth direction (Z-axis direction shown in FIG. 1) of the living tissue 101 under the control of, for example, the scan unit 3.

The light radiated from the radiation/reception unit 2 is reflected at a position, which is one position located in the depth direction (Z-axis direction shown in FIG. 1) of the living tissue 101, corresponding to the area at which the ultrasound wave converges. The reflected light passes through the opening of the ultrasound transducer 26 and the acoustic lens 26a, then enters the half mirror 22 as object light. That is, the light transmitted through the half mirror 22 is reflected at the area (the portion influenced by the ultrasound wave) whose density is increased by the ultrasound wave and then enters the half mirror 22 as object light.

The half mirror 22 allows the reference light coming from the reference mirror 25 to interfere with the object light coming from the ultrasound transducer 26, so that interference light, which is caused by the interference between the two fluxes of light, is radiated toward the light detector 27.

The light detector 27 applies heterodyne detection to the interference light coming from the half mirror 22, and converts the detected interference light into an interference signal, which is an electric signal. The light detector 27 outputs the interference signal to the signal processor 6.

The scan unit 3 is configured to, in response to each scan signal issued from the scan signal generator 9, change the spatial position of the ultrasound transducer 26 and the acoustic lens 26a, that is, the spatial position of the unit 2 (i.e., scan position) in the X-axis or Y-axis direction shown in FIG. 1.

The driving signal generator 4 produces an ultrasound wave drive signal for making the ultrasound transducer 26 radiate a predetermined ultrasound wave having a predetermined wavelength (or a predetermined frequency), and outputs the produced ultrasound wave drive signal to the amplifier 5. The driving signal generator 4 outputs a light source drive signal for driving the light source 21 to the light source 21 at the timing when a control signal is inputted from the signal processor 6. The light source 21 changes the wavelength of light to be radiated to the living tissue 101 from one wavelength to another wavelength in response to the light source drive signal. Furthermore, when the scan position of the scan unit 3 reaches the end position of the scan range of the scan unit 3, the driving signal generator 4 outputs a trigger signal to the signal processor 6.

The amplifier 5 comprises a power amplifier. This amplifier 5 amplifies the power of the ultrasound wave drive signal outputted from the driving signal generator 4, and provides the amplified ultrasound wave drive signal to the ultrasound transducer 26.

The signal processor 6 comprises a computing section 6a, which performs calculation and the like, and a memory 6b, which stores data such as calculation results of the computing section 6a.

The computing section 6a is provided with a spectrum analyzer or a digital oscilloscope (not shown). The computing sector 6a receives a first interference signal which is outputted from the light detector 27 after the light having one wavelength is emitted at one scan position. The computing section 6a calculates the signal level of the first interference signal which is a value corresponding to light intensity of the interference light. Then, the computing section 6a writes the calculated signal level into the memory 6b. In addition, the computing section 6a outputs a control signal to the driving signal generator 4 at the timing when the calculated signal level of the first interference signal is written into the memory 6b. The control signal is outputted to make the light source 21 change the wavelength of light radiated to the living tissue 101.

Thereafter, the computing section 6a receives a second interference signal which is outputted from the light detector 27 after the light having another wavelength is emitted at the same scan position. The computing section 6a calculates the signal level of the second interference signal which is a value corresponding to light intensity of the interference light. Then, the computing section 6a applies FFT (fast Fourier transformation) to the difference value between the signal level of the first interference signal and the signal level of the second interference signal, thereby calculating a variation of the Doppler shift amount (i.e., the amount of frequency modulation) at the scan position, which is characteristic information indicative of internal states of the living tissue. The calculation of the variation of the Doppler shift amount will be described in detail later.

Furthermore, the computing section 6a applies an arithmetic operation to the variation of the Doppler shift amount to produce image data at the scan position. The computing section 6a relates the produced image data to scan positional information which shows positions within a scan range (X-axis and Y-axis directions) where the scan can be performed by the scan unit 3, and stores the image data and the scan positional information, which are related to each other, in the memory 6b.

When the scan position is not the end position of the scan range of the scan unit 3 (that is, when the whole scan is not completed), the computing section 6a controls the scan signal generator 9 to change the scan position from the current scan position to another scan position (in the X-axis or Y-axis direction shown in FIG. 1). In addition, the computing section 6a outputs a control signal to the driving signal generator 4 to change the wavelength of light radiated to the living tissue 101.

When the computing section 6a detects a state in which the scan is completed based on a trigger signal outputted from the driving signal generator 4, the computing section 6a performs mapping to produce image data for one frame. The mapping is performed by using the image data and the scan positional information related to the image data, which are stored in the memory 6b between the time when the previous trigger signal is inputted and the time when the current trigger signal is inputted. The computing section 6a converts the image data for one frame into a video signal and outputs the video signal to the display unit 8. Thereby, the display unit 8 displays an image (tomographic image) inside the living tissue 101 in a plane such as the X-Z plane shown in FIG. 1.

The scan signal generator 9 provides scan signals to the scan unit 3 under the control of the signal processor 6 to radiate the ultrasound wave and the light while changing the scan position.

Figure 3:
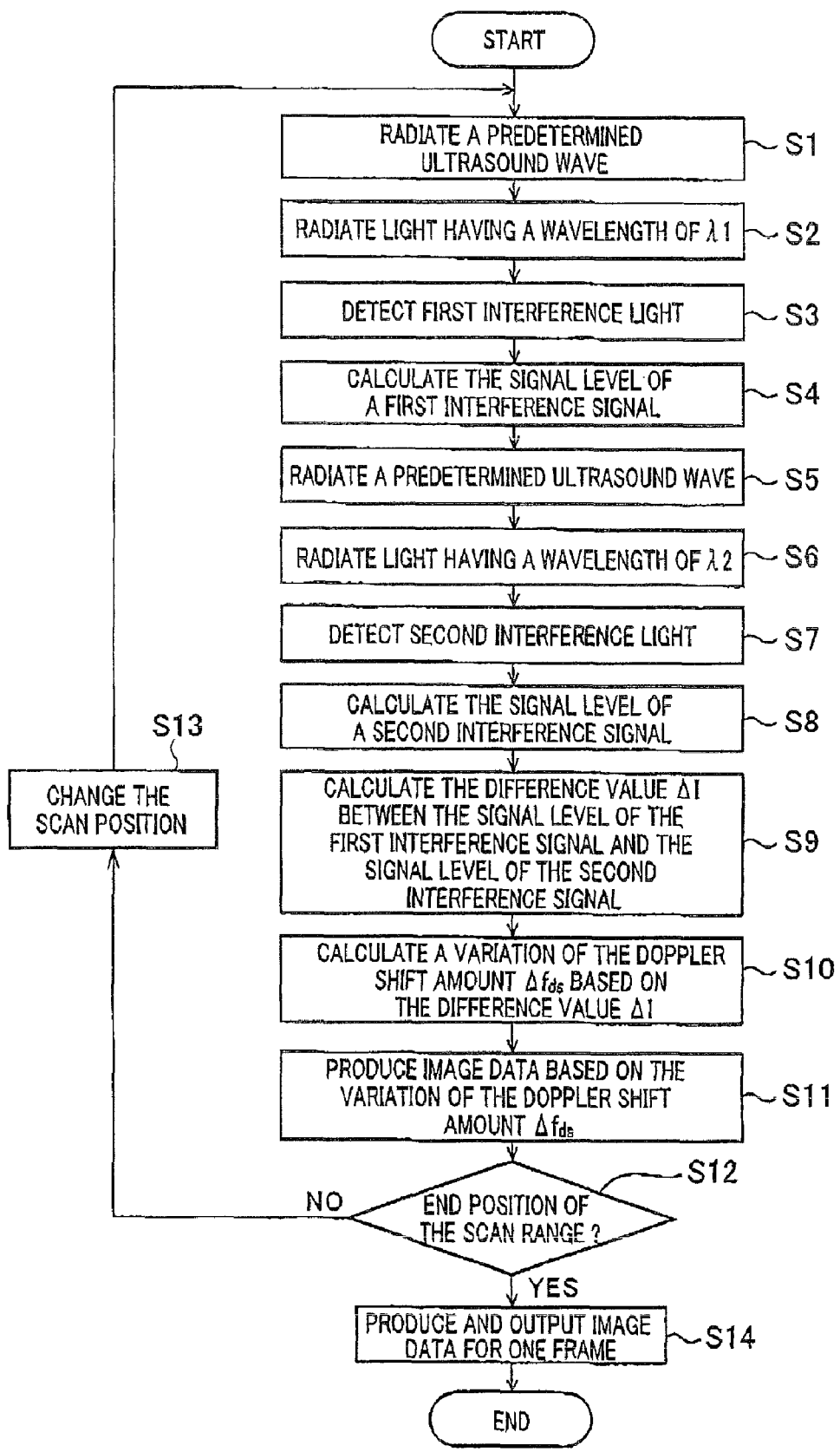
FIG. 3 is a flowchart showing an example of a process performed in the biological observation apparatus shown in FIG. 1.

Next, operations of the biological observation apparatus 1 according to the first embodiment will now be described with reference to a flowchart shown in FIG. 3.

First, an operator powers up each part of the biological observation apparatus 1, and positions the ultrasound transducer 26 (and the acoustic lens 26a) of the radiation/reception unit 2 such that ultrasound waves and light are radiated in the Z-axis direction shown in FIG. 1 (i.e., the depth direction of the living tissue 101) at one scan position (a position in X-axis and Y-axis directions). Concurrently, a space between the acoustic lens 26a and the living tissue 101 is filled with an ultrasound transmissive medium UM, for example, water.

The operator then turns on switches, which are mounted in an operation device (not shown), to instruct the apparatus 1 to start obtaining biological information of the living tissue 101.

The driving signal generator 4 outputs an ultrasound wave drive signal for radiating a predetermined ultrasound wave to the ultrasound transducer 26 via the amplifier 5 in response to the instruction.

In step S1, the ultrasound transducer 26 and the acoustic lens 26a radiate a predetermined ultrasound wave, in accordance with the ultrasound wave drive signal received from the amplifier 5, in the direction in which light is radiated and toward the living tissue 101. Thereby, the ultrasound wave radiated from the ultrasound transducer 26 and the acoustic lens 26a travels inside the living tissue 101 as a cyclic compressional wave. The ultrasound wave converges at a position of $z=Z_0$, which corresponds to a predetermined area located in the depth direction (Z-axis direction shown in FIG. 1) of the living tissue 101.

Meanwhile, the driving signal generator 4 generates a light source drive signal for making the unit 2 emit the light of wavelength $\lambda 1$ in response to the instruction, and outputs the light source drive signal to the light source 21.

In step S2, the light source 21 radiates the light of wavelength $\lambda 1$ to the half mirror 22 based on the light source drive signal received from the driving signal generator 4.

The light of wavelength $\lambda 1$ and emitted from the light source 21 is radiated to the reference mirror 25 via the half mirror 22 and is also radiated in the Z-axis direction (the depth direction of the living tissue 101) through the opening formed at the center of the ultrasound transducer 26 and the acoustic lens 26a.

The light of wavelength $\lambda 1$ and radiated into the living tissue 101 is reflected from the position of $Z=Z_0$. The reflected light passes through the opening of the ultrasound transducer 26 and the acoustic lens 26a and enters the half mirror 22 as object light.

The object light coming from the ultrasound transducer 26 interferes with the reference light coming from the reference mirror 25 in the half mirror 22 and enters the light detector 27 as first interference light.

In step S3, the light detector 27 applies heterodyne detection to the first interference light coming from the half mirror 22, and converts the detected first interference light into a first interference signal, which is an electrical signal. The light detector 27 outputs the first interference signal to the signal processor 6.

Hereinafter, a case is considered in which a position located in the depth direction (Z-axis direction shown in FIG. 1) of one scan position is defined as $Z=Z_0$, and a blood vessel having a thickness (diameter) of d, which is a light absorber, exists in a position of the surface side with respect to the position of $Z=Z_0$ (that is, $Z<Z_0$). In this case, the intensity of the light of wavelength $\lambda 1$ exponentially decreases with the increase of the thickness of d, as shown in, for example, $A(\lambda 1)$ of the following expression (1).

$$A(\lambda 1) = \exp(-\alpha(\lambda 1) \cdot d) \quad (1)$$

Note that $\alpha(\lambda 1)$ in the expression (1) is defined as a constant obtained by substituting a wavelength of $\lambda 1$ into $\lambda$ of a predetermined function $\alpha(\lambda)$. If no blood vessel, which is a light absorber, exists in a position of the surface side with respect to the position of $Z=Z_0$ located in the depth direction, the thickness of d is defined as 0.

$A(\lambda 1)$ of the expression (1) is a value by which the alternating-current component of the signal level of the first interference signal is multiplied. Therefore, in step S4, the computing section 6a defines the direct-current component of the first interference signal as DC. The computing section 6a defines the amplitude of the alternating-current component of the first interference signal as $m(Z_0)$ in a case where there is no blood vessel, which is a light absorber, existing toward the surface side with respect to the position of $Z=Z_0$ located in the depth direction. The computing section 6a also defines the phase of the light of wavelength $\lambda 1$ as $\phi 1$. The computing section 6a calculates the signal level of the first interference signal, which is a value corresponding to light intensity of the first interference light, as $I(\lambda 1, Z_0)$ shown by the following expression (2).

$$I(\lambda 1, Z_0) = DC + A(\lambda 1) \cdot m(Z_0) \cos\{2\pi\Delta f(\lambda 1) \cdot t + \phi 1\} \quad (2)$$

The computing section 6a writes the solution of the expression (2) which is the signal level of the first interference signal, which is a value corresponding to light intensity of the first interference light, into the memory 6b. Then, the computing section 6a outputs a control signal for changing the wavelength of light radiated to the living tissue 101 to the driving signal generator 4 at the timing when the solution of the expression (2) is written into the memory 6b.

The driving signal generator 4 outputs an ultrasound wave drive signal for radiating a predetermined ultrasound wave to the ultrasound transducer 26 via the amplifier 5 at the timing when the control signal is inputted from the signal processor 6. The driving signal generator 4 then outputs a light source drive signal for changing the wavelength of the light radiated to the living tissue 101 from $\lambda 1$ to $\lambda 2$.

In step S5, the ultrasound transducer 26 and the acoustic lens 26a radiate a predetermined ultrasound wave, in accordance with the ultrasound wave drive signal received from the amplifier 5, in the direction in which light is radiated and toward the living tissue 101. In step S6, the light source 21 radiates the light of wavelength $\lambda 2$ to the half mirror 22 in response to the light source drive signal received from the driving signal generator 4.

The light of wavelength $\lambda 2$ and emitted from the light source 21 is radiated to the reference mirror 25 via the half mirror 22 and is also radiated in the Z-axis direction (the depth direction of the living tissue 101) through the opening formed at the center of the ultrasound transducer 26 and the acoustic lens 26a.

The light of wavelength $\lambda 2$ and radiated into the living tissue 101 is reflected from the position of $Z=Z_0$ as in the case of the light of wavelength $\lambda 1$. The reflected light passes through the opening of the ultrasound transducer 26 and the acoustic lens 26a and enters the half mirror 22 as object light.

The object light coming from the ultrasound transducer 26 interferes with the reference light coming from the reference mirror 25 in the half mirror 22 and enters the light detector 27 as second interference light.

In step S7, the light detector 27 applies heterodyne detection to the second interference light coming from the half mirror 22, and converts the detected second interference light into a second interference signal, which is an electrical signal. The light detector 27 outputs the second interference signal to the signal processor 6.

In this case, the intensity of the light of wavelength $\lambda 2$ exponentially decreases with the increase of the thickness of d, as shown in, for example, $A(\lambda 2)$ of the following expression (3).

$$A(\lambda 2) = \exp(-\alpha(\lambda 2) \cdot d) \quad (3)$$

Note that $\alpha(\lambda 2)$ in the expression (3) is defined as a constant obtained by substituting a wavelength of $\lambda 2$ into $\lambda$ of the predetermined function $\alpha(\lambda)$ described above. If there is no blood vessel, which is a light absorber, existing toward the surface side with respect to the position of $Z=Z_0$ located in the depth direction, the thickness of d is defined as 0.

$A(\lambda 2)$ of the expression (3) is a value by which the alternating-current component of the signal level of the second interference signal is multiplied. Therefore, in step S8, the computing section 6a defines the direct-current component of the second interference signal as DC. The computing section 6a defines the amplitude of the alternating-current component of the second interference signal as $m(Z_0)$ in a case where there is no blood vessel, which is a light absorber, existing toward the surface side with respect to the position of $Z=Z_0$ located in the depth direction. The computing section 6a also defines the phase of the light of wavelength $\lambda 2$ as $\phi 2$. The computing section 6a calculates the signal level of the second interference signal, which is a value corresponding to light intensity of the second interference light, as $I(\lambda 2, Z_0)$ shown by the following expression (4).

$$I(\lambda 2, Z_0) = DC + A(\lambda 2) \cdot m(Z_0) \cos\{2\pi\Delta f(\lambda 2) \cdot t + \phi 2\} \quad (4)$$

The function $\alpha(\lambda)$ is a function showing the wavelength dependency of the absorptivity of the blood, that is, a function which corresponds to the shape of a graph shown in FIG. 2. Therefore, the value of $\alpha(\lambda)$ corresponds with the value obtained by scaling the graph shown in FIG. 2 with a constant value.

In addition, the wavelengths $\lambda 1$ and $\lambda 2$ of the light emitted from the light source 21 are selected from a range from 800 nm to 930 nm, where sensitivity with respect to any change of oxygen saturation in the blood is low and absorbance (molar absorptivity) of the wavelengths $\lambda 1$ and $\lambda 2$ becomes approximately equal to each other. In consequence, the value of constant $\alpha(\lambda 1)$ shown in the expression (1) is approximately equal to the value of constant $\alpha(\lambda 2)$ shown in the expression (3).

Accordingly, when assuming that $\alpha(\lambda 1)=\alpha(\lambda 2)$, the value of the right side of the expression (1) and the value of the right side of the expression (3) are equal to each other. Furthermore, when assuming that $A(\lambda 1)=A\alpha(\lambda 2)=A_0$, the expressions (2) and (4) can be rewritten as the following expressions (5) and (6).

$$I(\lambda 1, Z_0) = DC + A_0 \cdot m(Z_0) \cos\{2\pi\Delta f(\lambda 1) \cdot t + \phi 1\} \quad (5)$$

$$I(\lambda 2, Z_0) = DC + A_0 \cdot m(Z_0) \cos\{2\pi\Delta f(\lambda 2) \cdot t + \phi 2\} \quad (6)$$

Accordingly, in step S9, the computing section 6a calculates the difference value $\Delta I$ between the solution of the expression (5) and the solution of the expression (6) as shown in the following expression (7) with reference to the data stored in the memory 6a.

$$\Delta I = I(\lambda 1, Z_0) - I(\lambda 2, Z_0)$$
$$= A_0 \cdot m(Z_0)[\cos\{2\pi\Delta f(\lambda 1) \cdot t + \phi 1\} - \cos\{2\pi\Delta f(\lambda 2) \cdot t + \phi 2\}] \quad (7)$$

Then, in step S10, the computing section 6a applies FFT (fast Fourier transformation) to the right side of the expression (7), thereby calculating a variation of the Doppler shift amount $\Delta f_{ds}$ at one area (one position located in the Z-axis direction) of one scan position as shown in the following expression (8).

$$\Delta f_{ds} = \Delta f(\lambda 1) - \Delta f(\lambda 2) \quad (8)$$

Note that $\Delta f(\lambda 1)$ shown in the expression (8) is defined as the Doppler shift amount generated when the light of wavelength $\lambda 1$ is reflected at a position of $Z=Z_0$ located in the depth direction. In addition, $\Delta f(\lambda 2)$ shown in the expression (8) is defined as the Doppler shift amount generated when the light of wavelength $\lambda 2$ is reflected at one area of one scan position.

Meanwhile, the velocity of a predetermined ultrasound wave radiated from the ultrasound transducer 26 and the acoustic lens 26a is defined as $V_{us}$. The wavelength of the predetermined ultrasound wave is defined as $\lambda_{us}$. The index of refraction of tumor tissue is defined as $n(\lambda)$ when the light of wavelength of $\lambda 1$ enters the tumor tissue. The amount of change in the index of refraction generated depending on the radiated ultrasound wave is defined as $\Delta n(\lambda)$. In this case, the Doppler shift amounts $\Delta f(\lambda 1)$ and $\Delta f(\lambda 2)$ are shown by the following expressions (9) and (10).

$$\Delta f(\lambda 1) = \{2V_{us}(n(\lambda 1) + \Delta n(\lambda 1))\}/\lambda_{us} \quad (9)$$

$$\Delta f(\lambda 2) = \{2V_{us}(n(\lambda 2) + \Delta n(\lambda 2))\}/\lambda_{us} \quad (10)$$

Then, the computing section 6a substitutes the expressions (9) and (10) into the expression (8) and divides the expression (8) by $\lambda_{us}/2V_{us}$, thereby obtaining the following expression (11).

$$\Delta f_{ds} \cdot (\lambda_{us}/2V_{us}) = (n(\lambda 1) + \Delta n(\lambda 1)) - (n(\lambda 2) + \Delta n(\lambda 2)) \quad (11)$$

In step S11, the computing section 6a assumes the value of the right side of the expression (11), which is a value obtained by subtracting the amount of change in the index of refraction of tumor tissue generated when the light of wavelength $\lambda 2$ is emitted from the amount of change in the index of refraction of the tumor tissue generated when the light of wavelength $\lambda 1$ is emitted, as a pixel value of one area of one scan position, and produces image data of the one area of the one scan position. Then, the computing section 6a relates the produced image data to scan positional information, which shows positions within a scan range where the scan can be performed by the scan unit 3, and positional information in the Z-axis direction, and stores the image data, the scan positional information, and the positional information in the Z-axis direction in the memory 6b.

The operations of the steps S1 to S11 are performed multiple times while changing the position, at which the ultrasound wave converges, in the depth direction (Z-axis direction shown in FIG. 1) of the living tissue 101 (that is, $z=Z_0$, Z1, Z2, ...) by the acoustic lens 26a under the control of the signal processor 6.

In step S12, the computing section 6a determines whether or not the current scan position at which the image data is obtained is the end position of the scan range of the scan unit 3. When the current scan position at which the image data is obtained is not the end position of the scan range of the scan unit 3 (that is, when the whole scan is not completed), in step S13, the computing section 6a controls the scan signal generator 9 to change the scan position from the current scan position to another scan position (in the X-axis or Y-axis direction shown in FIG. 1). In addition, the computing section 6a outputs a control signal to the driving signal generator 4 to change the wavelength of light radiated to the living tissue 101. Thereafter, each part of the biological observation apparatus 1 repeats the above-described operations until the computing section 6a determines, in step S12, that the current scan position is the end position of the scan range of the scan unit 3.

Thereafter, when the computing section 6a detects a state in which the scan is completed based on a trigger signal outputted from the driving signal generator 4, in step S14, the computing section 6a performs mapping to produce image data for one frame. The mapping is performed by using the image data, and the scan positional information and the positional information in the Z-axis direction related to the image data, which are stored in the memory 6b between the time when the previous trigger signal is inputted and the time when the current trigger signal is inputted. The computing section 6a converts the image data for one frame into a video signal and outputs the video signal to the display unit 8. Thereby, based on the image data, the display unit 8 displays an image (tomographic image) inside the living tissue 101 in a plane such as an X-Z plane shown in FIG. 1.

Figure 4:
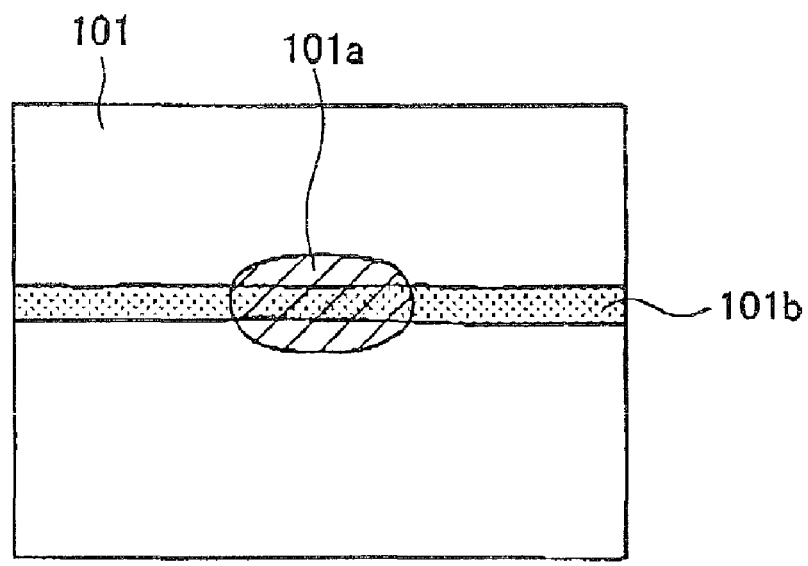
FIG. 4 is a diagram exemplifying a state of tumor tissue and a blood vessel existing in living tissue.
Figure 5:
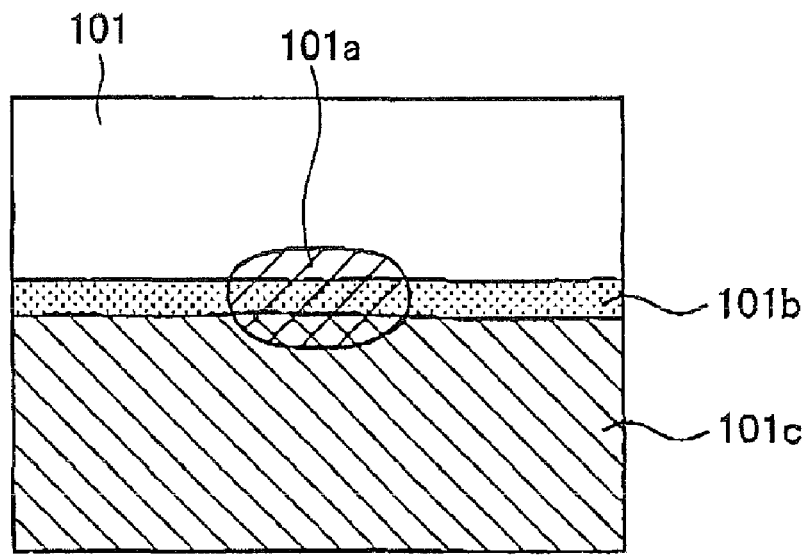
FIG. 5 is a diagram exemplifying a tomographic image produced based on the Doppler shift amount obtained by using light having a single wavelength.

FIG. 4 is a diagram exemplifying a state of tumor tissue and a blood vessel existing in living tissue. FIG. 5 is a diagram exemplifying a tomographic image produced based on the Doppler shift amount obtained by using the light having a single wavelength. When tumor tissue 101a and a blood vessel 101b exist in a state where they overlap with each other on the same cross-section as shown in FIG. 4 and the Doppler shift amount is obtained by using the light having a single wavelength, a tomographic image is produced based on the Doppler shift amount as shown in FIG. 5.

In the image shown in FIG. 5, part of the tumor tissue 101a is difficult to see due to the blood vessel 101b. In addition, since part of the light is absorbed by the blood vessel 101b, an area 101c deeper than the position at which the blood vessel 101b exists is blackened. Furthermore, in the image shown in FIG. 5, since the dynamic range of the information obtained based on the Doppler shift amount is narrow, the difference of brightness between an area corresponding to the boundary of the tumor tissue 101a and the other areas becomes small.

That is, when the Doppler shift amount is obtained by using the light having a single wavelength, and a tomographic image is produced based on the Doppler shift amount, a tomographic image in which the shape or the like of the tumor tissue 101 is difficult to identify is displayed on the display unit 8.

In contrast, in the biological observation apparatus 1, the blood vessel 101b is identified by using the light of wavelength λ1 and the light of wavelength λ2, which are two types of light matching the conditions described above. Then, the biological observation apparatus 1 calculates the difference between the Doppler shift amount obtained by using the light of wavelength λ1 and the Doppler shift amount obtained by using the light of wavelength λ2, thereby removing the image corresponding to the blood vessel 101b and the blackened image of the area 101c.

Figure 6:
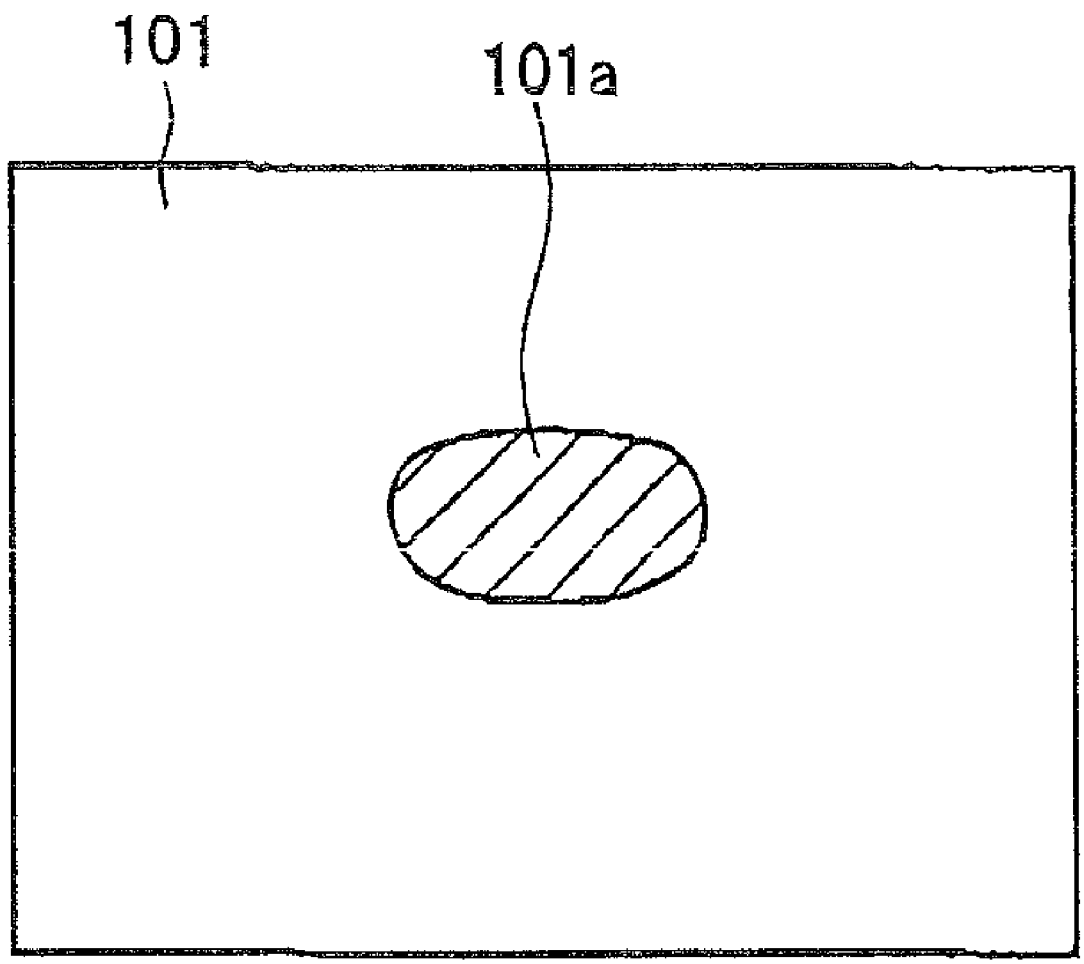
FIG. 6 is a diagram exemplifying a tomographic image obtained by the biological observation apparatus shown in FIG. 1.

FIG. 6 is a diagram exemplifying a tomographic image obtained by the biological observation apparatus shown in FIG. 1. The biological observation apparatus 1 having the configuration described above allows the dynamic range of the information obtained depending on the Doppler shift amount to be widened. Thereby, as shown in FIG. 6, a tomographic image in which the shape or the like of the tumor tissue 101a is easy to identify can be displayed on the display unit 8. In consequence, the biological observation apparatus 1 of the present embodiment can reduce the burden on the operator when observing tumor tissue.

In addition, even when the blood vessel 101b, which is a light absorber, exists in the scan range of the scan unit 3, the biological observation apparatus 1 having the configuration described above can detect light scattering information of the area 101c deeper than the position at which the blood vessel 101b exists with high accuracy.

Note that the angle of the direction in which the light is radiated and the angle of the direction in which the ultrasound wave is radiated are not limited to the same angle with respect to the living tissue 101, and may be different from each other with respect to the living tissue 101. In this case, for example, the ultrasound transducer 26 and the acoustic lens 26a may be disposed so that the direction in which the ultrasound wave is radiated is inclined with respect to the optical axis (Z-axis) of the light. Thereby, even when using an ultrasound wave composed of a continuous wave and light composed of a continuous wave, object light having no noise can be obtained from a predetermined area.

When applying the configuration described above to the biological observation apparatus 1 shown in FIG. 1, the area at which the ultrasound wave converges is changed in the depth direction of the living tissue 101 by moving the whole radiation/reception unit 2 in the Z-axis direction by the scan unit 3.

Figure 7:
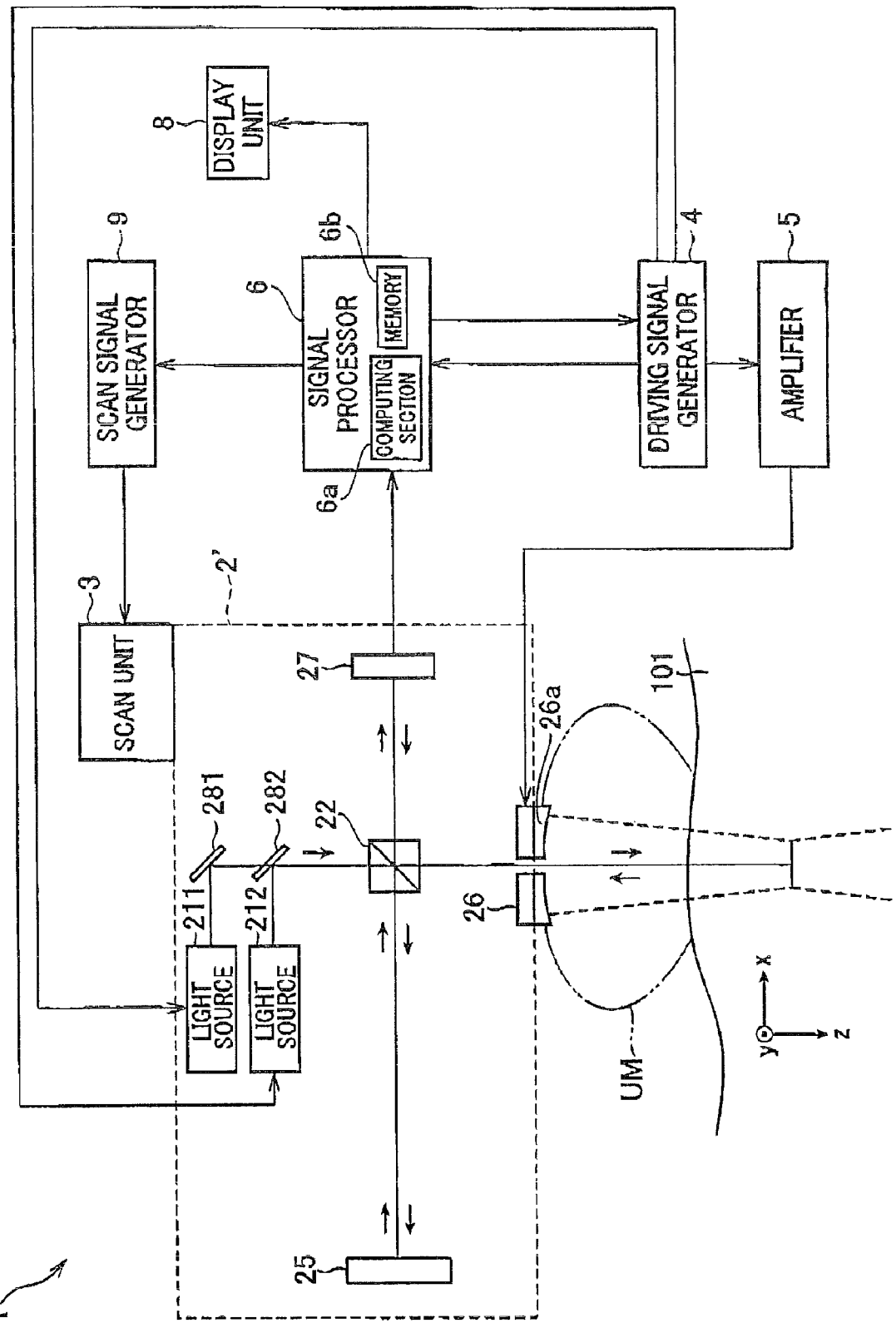
FIG. 7 is a diagram showing a modification of the biological observation apparatus shown in FIG. 1.

The biological observation apparatus 1 shown in FIG. 1 may be modified to a biological observation apparatus 1' shown in FIG. 7 which provides the same advantages as those of the biological observation apparatus 1 described above. The same reference numerals as in FIG. 1 denote the same parts in FIG. 7.

In FIG. 7, the light of wavelength λ1 and the light of wavelength λ2 are not emitted from the same light source and are emitted from two separate light sources, respectively. That is, in a radiation/reception unit 2' shown in FIG. 7, a light source 211 emits the light of wavelength λ1 and a light source 212 emits the light of wavelength λ2. The respective light sources 211 and 212 are composed of a laser diode (LD). Alternatively, the respective light sources 211 and 212 may be composed of a combination of a white light source or an SLD and a filter.

In this case, the driving signal generator 4 outputs a light source drive signal to the light source 211 or the light source 212 at the timing when a control signal is inputted from the signal processor 6 to make the light source 211 or the light source 212 emit light having a wavelength of λ1 or λ2, respectively. Light having a wavelength of λ1 emitted from the light source 211 is reflected at a mirror 281, passes through a mirror 282, and is radiated to the half mirror 22. Light having a wavelength of λ2 emitted from the light source 212 is reflected at a mirror 282 and is radiated to the half mirror 22.

Figure 8:
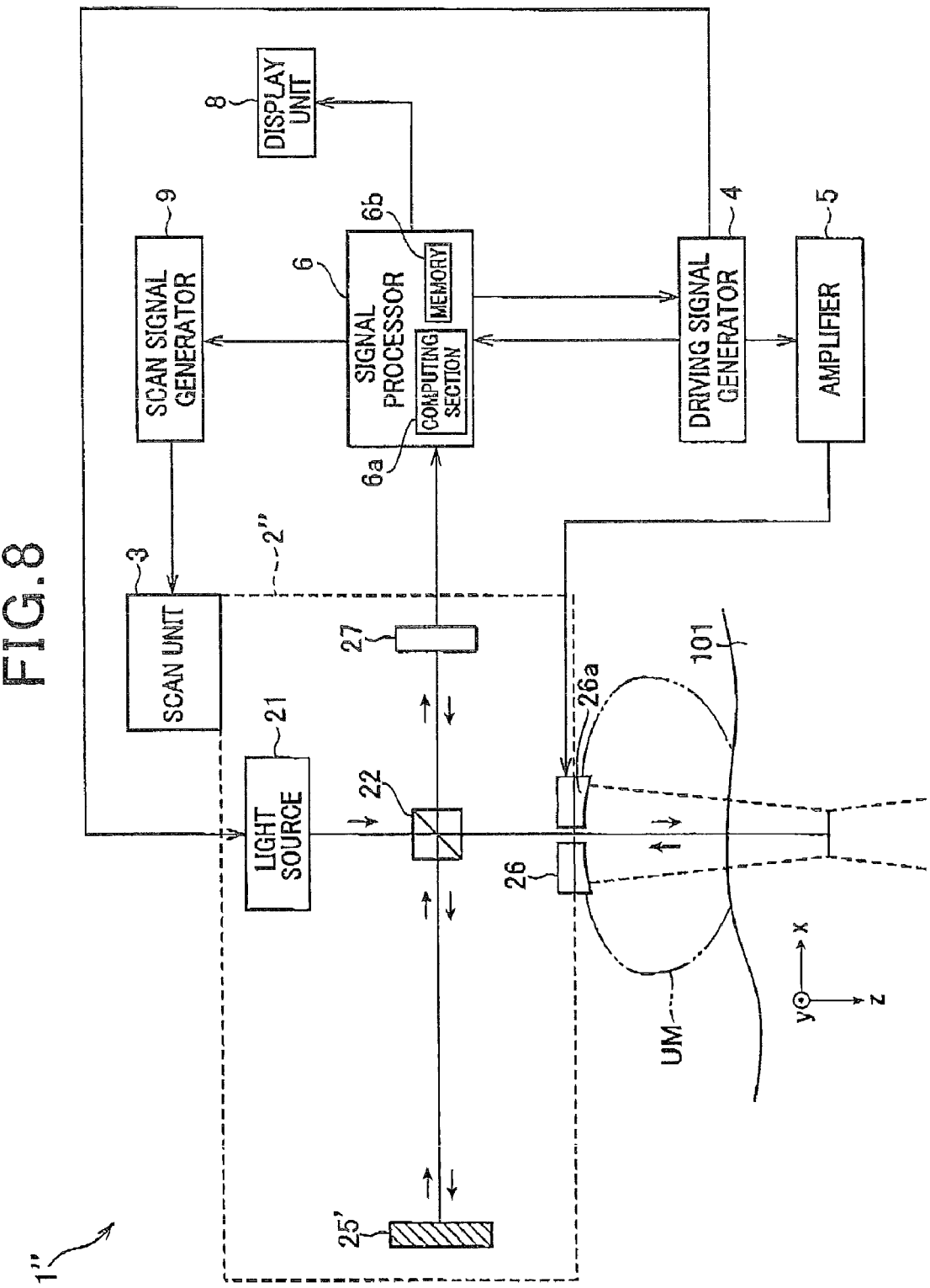
FIG. 8 is a diagram showing a modification of the biological observation apparatus shown in FIG. 1.

The biological observation apparatus 1 shown in FIG. 1 may be modified to provide a biological observation apparatus 1" shown in FIG. 8 which provides the same advantages as those of the biological observation apparatus 1 described above. According to the configuration, image data inside the living tissue 101 is produced without using the reference light described above, that is, without using the interference light. The same reference numerals as in FIG. 1 denote the same parts in FIG. 8.

In FIG. 8, a light absorber 25' composed of a board having a black color or the like is disposed instead of the reference mirror 25 shown in FIG. 1. Due to the configuration, the light emitted from the light source 21 and reflected at the half mirror 22 is absorbed in the light absorber 25'. Therefore, the light absorber 25' does not radiate the reference light. The light detector 27 detects only the object light reflected from the half mirror 22. This configuration can also obtain tomographic images by which the shape or the like of tumor tissue can be easily identified. Note that, instead of using the light absorber, a configuration in which the reference light does not enter the half mirror 22 may be employed.

Figure 9:
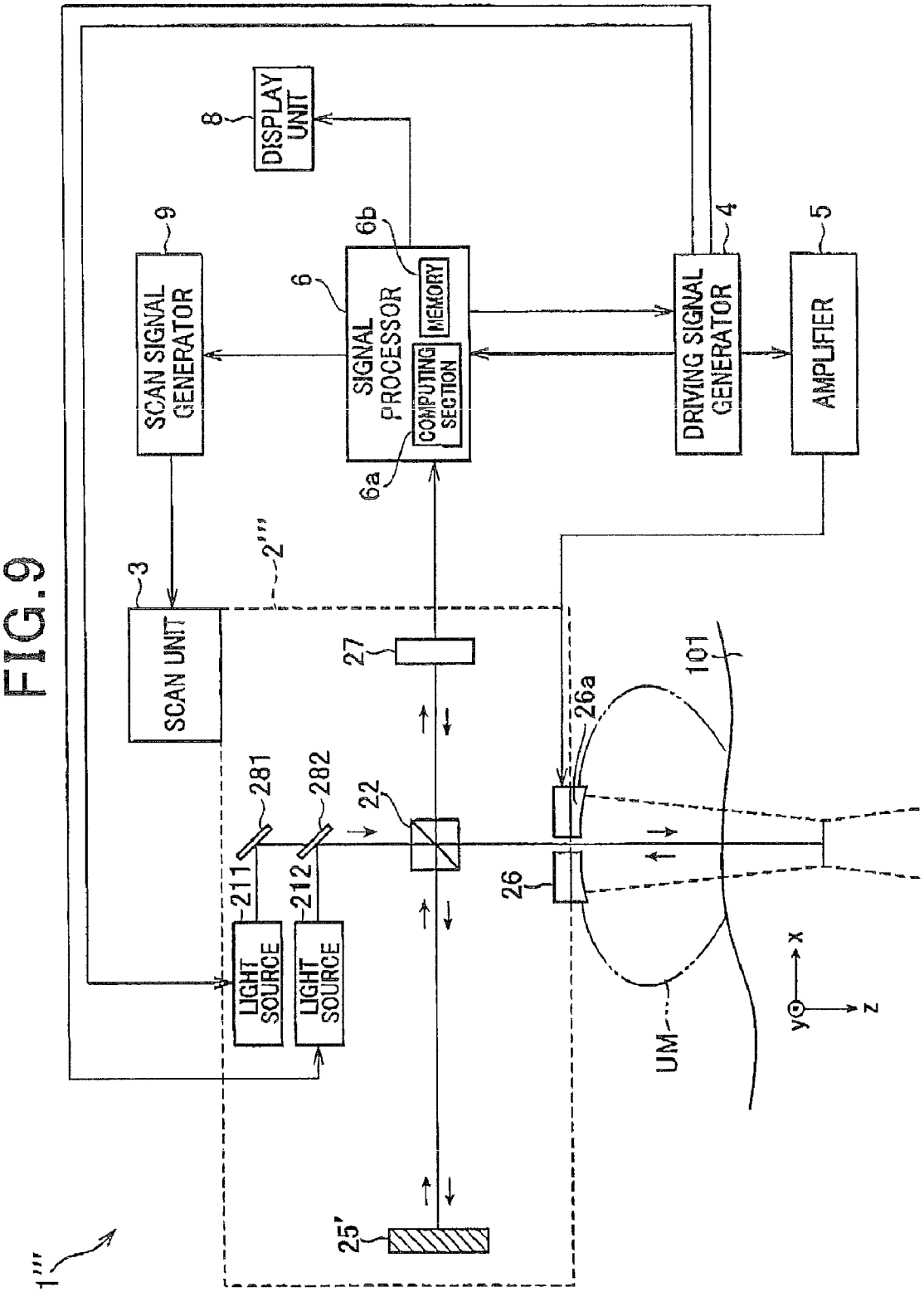
FIG. 9 is a diagram showing a modification of the biological observation apparatus shown in FIG. 1.

In addition, the biological observation apparatus 1' shown in FIG. 7 may be modified to provide a biological observation apparatus 1''' shown in FIG. 9 in which the light absorber 25' composed of a board having a black color or the like is disposed instead of the reference mirror 25.

Figure 10:
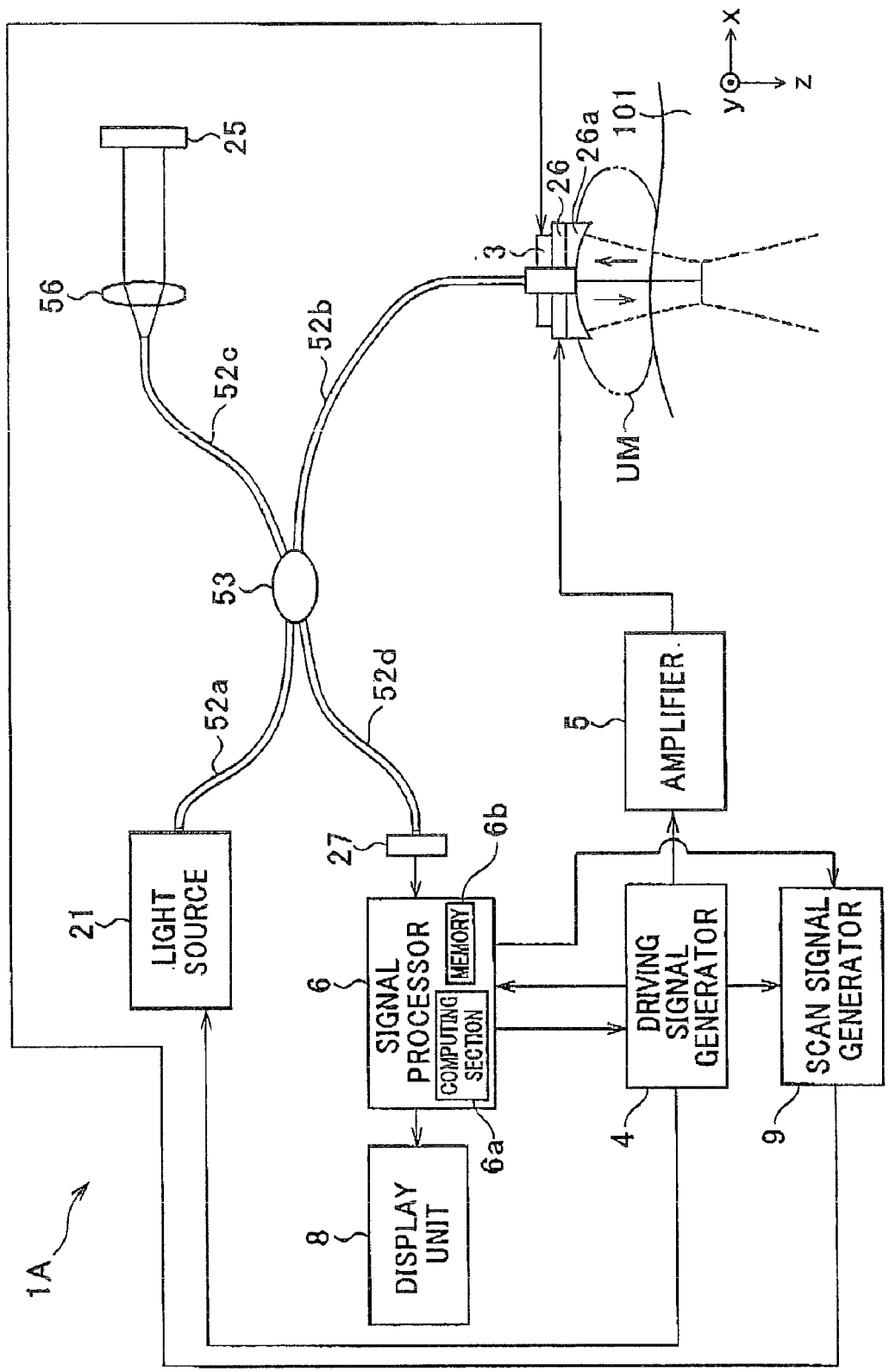
FIG. 10 is a diagram showing a modification of the biological observation apparatus shown in FIG. 1 according to the first embodiment of the present invention.

The biological observation apparatus 1 shown in FIG. 1 may be modified to provide a biological observation apparatus 1A shown in FIG. 10 which provides the same advantages as those of the biological observation apparatus 1 described above. The same reference numerals as in FIG. 1 denote the same parts in FIG. 10.

Specifically, the biological observation apparatus 1A includes a scan unit 3, a driving signal generator 4, an amplifier 5, a signal processor 6, a display unit 8, a scan signal generator 9, a light source 21, a reference mirror 25, an ultrasound transducer 26, an acoustic lens 26a, and a light detector 27, as well as optical fibers 52a, 52b, 52c, and 52d, an optical coupler 53, and a collimating lens 56, which are main parts.

Figure 11:
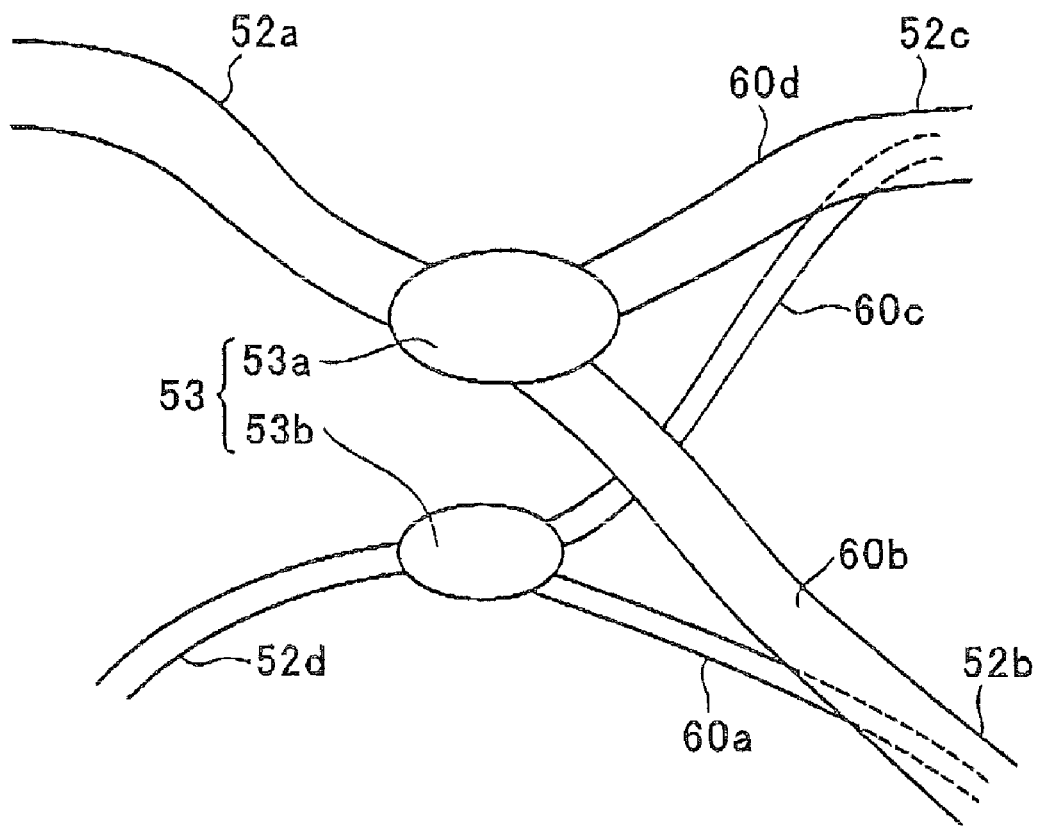
FIG. 11 is a diagram showing a configuration of an optical coupler in detail.

In addition, the optical coupler 53 comprises, as shown in FIG. 11, a first coupler 53a and a second coupler 53b.

The optical fiber 52a has one end (first end) connected to the light source 21 and the other end (second end) connected to the first coupler 53a, as shown in FIGS. 10 and 11.

Figure 12:
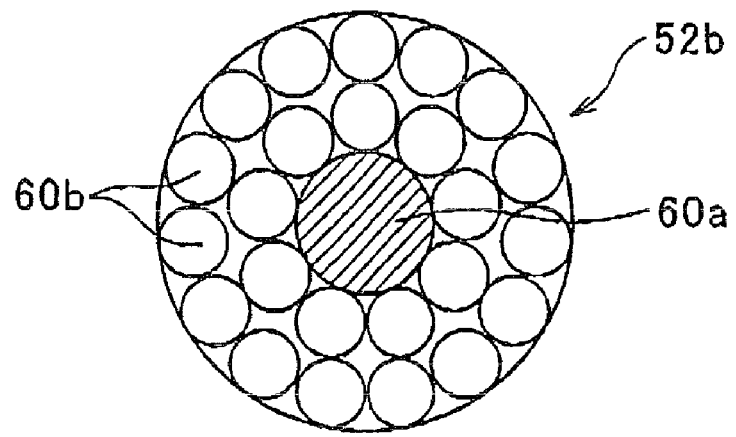
FIG. 12 is a sectional diagram exemplifying a configuration of an end part of an optical fiber.

The optical fiber 52b comprises, as shown in FIG. 11, a light-receiving fiber bundle 60a and a light-sending fiber bundle 60b. The fiber bundle 60a has one end (first end) connected to the second coupler 53b and the other end (second end) connected to the openings (not shown) formed at the center of the ultrasound transducer 26 and the acoustic lens 26a in such a manner that the other end (second end) is inserted therethrough. Meanwhile, the fiber bundle 60b has one end (first end) connected to the first coupler 53a and the other end (second end) connected to the openings formed at the center of the ultrasound transducer 26 and the acoustic lens 26a in such a manner that the other end (second end) is inserted therethrough. Both the other ends (second ends) of the fiber bundles 60a and 60b are arranged at the openings of the ultrasound transducer 26 and the acoustic lens 26a as illustrated in FIG. 12. In FIG. 12, the fiber bundle 60a is adapted to a core and surrounded by the fiber bundle 60b.

The optical fiber 52c comprises, as shown in FIG. 11, a light-receiving fiber bundle 60c and a light-sending fiber bundle 60d. The fiber bundle 60c has one end (first end) connected to the second coupler 53b and the other end (second end) arranged at a position where the light can enter from the collimating lens 56. Moreover, the fiber bundle 60d has one end (first end) connected to the first coupler 53a and the other end (second end) arranged at a position where the light can be radiated to the collimating lens 56.

The optical fiber 52d has, as shown in FIGS. 10 and 11, one end (first end) connected to the second coupler 53b and the other end (second end) connected to the light detector 27.

According to the configuration described above, in the biological observation apparatus 1A, the light of wavelength λ1 emitted from the light source 21 is radiated to the living tissue 101 via the optical fiber 52a, the first coupler 53a, and the fiber bundle 60b and to the collimating lens 56 via the optical fiber 52a, the first coupler 53a, and the fiber bundle 60d.

The light which enters the collimating lens 56 is converted to parallel-flux light and radiated to the reference mirror 25. This light is reflected from the reference mirror 25. The reflected light passes through the collimating lens 56 again, and enters the fiber bundle 60c as reference light. This reference light incident on the fiber bundle 60c is then radiated to the second coupler 53b.

Meanwhile, the light of wavelength λ1 and radiated into the living tissue 101 via the fiber bundle 60b travels inside the living tissue 101 in the depth direction (Z-axis direction shown in FIG. 10). The light reaches a portion corresponding to the area where the predetermined ultrasound wave radiated from the ultrasound transducer 26 and the acoustic lens 26a converges. The light is reflected from the portion. The light reflected from the portion enters the fiber bundle 60a as object light.

In the second coupler 53b, the object light coming from the fiber bundle 60a interferes with the reference light coming from the fiber bundle 60c, thereby producing first interference light. The first interference light enters the light detector 27 via the optical fiber 52d.

The signal processor 6 then applies the same process as performed by the biological observation apparatus 1 (the process based on the expressions (1) and (2)) to the first interference signal outputted from the light detector 27. Thereby, the signal level of the first interference signal, which is a value corresponding to light intensity of the first interference light, is calculated and then written into the memory 6b.

After the calculation of the value of the signal level of the first interference signal is completed, a control signal is outputted from the signal processor 6, and the light of wavelength λ2 is radiated from the light source 21 into the living tissue 101 via the path described above.

The light of wavelength λ2 and radiated into the living tissue 101 is reflected at the same portion as that at which the light of wavelength λ1 is reflected. The light reflected from the portion enters the fiber bundle 60a as object light. This object light incident on the fiber bundle 60a is then radiated to the second coupler 53b.

In the second coupler 53b, the object light coming from the fiber bundle 60a interferes with the reference light coming from the fiber bundle 60c, thereby producing second interference light. The second interference light enters the light detector 27 via the optical fiber 52d.

The signal processor 6 then applies the same process as that of the biological observation apparatus 1 (the process based on the expressions (3) and (4)) to the second interference signal outputted from the light detector 27. Thereby, the signal level of the second interference signal, which is a value corresponding to light intensity of the second interference light, is calculated.

Then, processes based on the expressions (5) to (11) are subsequently performed in series, thereby producing image data for one pixel corresponding to one position located in the Z-axis direction of one scan position. Furthermore, the process for producing image data for one pixel is repeated until the scan position reaches the end position of the scan range. Thereby, the image data for one frame is produced and converted into the video signal, and the video signal is outputted to the display unit 8.

The biological observation apparatus 1A shown in FIG. 10 having the configuration described above provides the same advantages as those of the biological observation apparatus 1 described above.

Figure 13:
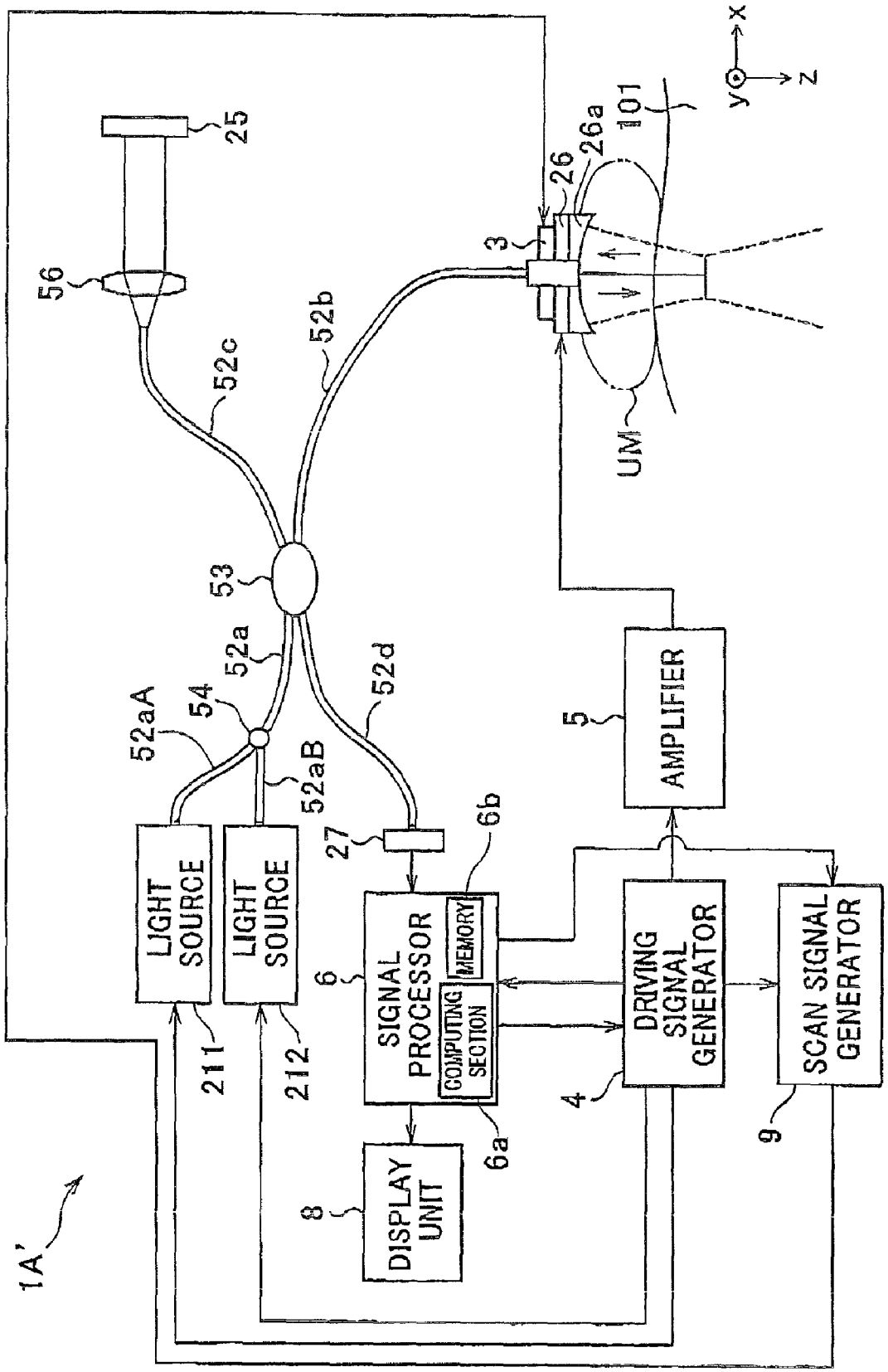
FIG. 13 is a diagram showing a modification of the biological observation apparatus shown in FIG. 10.

The biological observation apparatus 1A shown in FIG. 10 may be modified to a biological observation apparatus 1A' shown in FIG. 13 which provides the same advantages as those of the biological observation apparatus 1 described above. The same reference numerals as in FIG. 10 denote the same parts in FIG. 13.

In FIG. 13, the light of wavelength λ1 and the light of wavelength λ2 are not emitted from the same light source and are emitted from two separate light sources, respectively. That is, in the same manner as in FIG. 7, in the apparatus 1A' shown in FIG. 13, the light source 211 emits light having a wavelength of λ1 and the light source 212 emits light having a wavelength of λ2. The light of wavelength λ1 emitted from the light source 211 enters the optical coupler 53 via an optical fiber 52aA, an optical coupler 54, and the optical fiber 52a. The light of wavelength λ2 emitted from the light source 212 enters the optical coupler 53 via an optical fiber 52aB, an optical coupler 54, and the optical fiber 52a.

Figure 14:
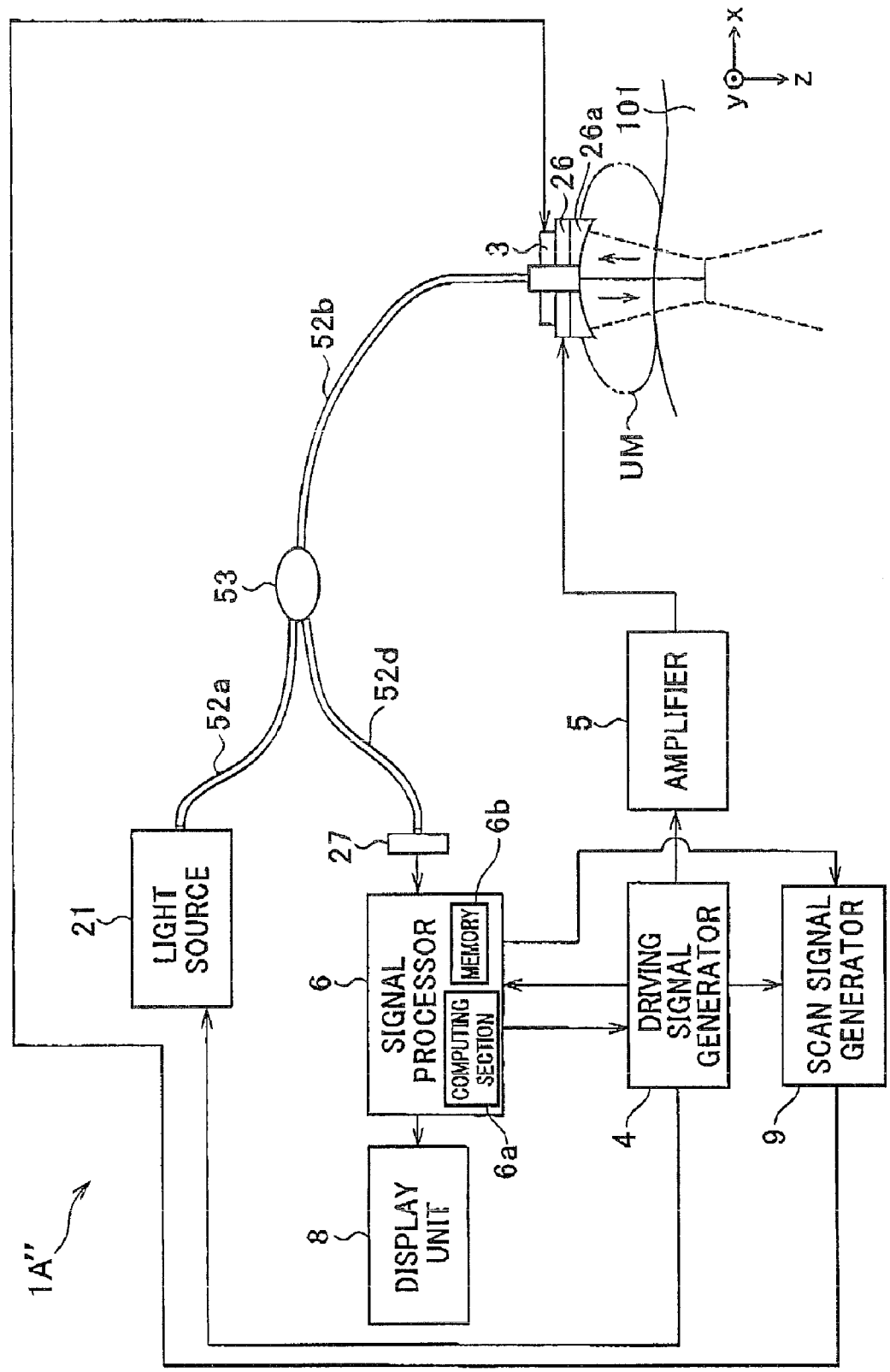
FIG. 14 is a diagram showing a modification of the biological observation apparatus shown in FIG. 10.

The biological observation apparatus 1A shown in FIG. 10 may be modified to a biological observation apparatus 1A" shown in FIG. 14 which provides the same advantages as those of the biological observation apparatus 1 described above. According to the configuration, image data inside the living tissue 101 is produced without using the reference light described above, that is, without using the interference light. The same reference numerals as in FIG. 10 denote the same parts in FIG. 14.

In FIG. 14, the optical fiber 52c, the collimating lens 56, and the reference mirror 25 shown in FIG. 10 are removed. Due to the configuration, the reference light does not enter the optical coupler 53. The light detector 27 detects only the object light from the optical coupler 53. This configuration can also obtain tomographic images by which the shape or the like of tumor tissue can be easily identified.

In addition, the biological observation apparatus 1A' shown in FIG. 13 may be modified to a biological observation apparatus 1A''' shown in FIG. 15 in which the optical fiber 52c, the collimating lens 56, and the reference mirror 25 are removed.

Referring to FIGS. 16 and 17, a biological observation apparatus according to the second embodiment of the present invention will now be described.

Hereinafter, explanations of parts having the same configuration as those of the first embodiment will be omitted. The biological observation apparatus of the second embodiment has a configuration similar to that of the biological observation apparatus of the first embodiment. For this reason, in the second embodiment, parts which are different from those of the biological observation apparatus of the first embodiment will be mainly described.

FIG. 16 outlines a biological observation apparatus 1B. The same reference numerals as in FIG. 1 denote the same parts in FIG. 16. This biological observation apparatus 1B comprises, as shown in FIG. 16, the radiation/reception unit 2, the scan unit 3, the driving signal generator 4, the amplifier 5, a signal processor 6A, the display unit 8, and the scan signal generator 9, which are main parts. The signal processor 6A comprises the computing section 6a, the memory 6b, and a determination section 6c.

The determination section 6c determines whether a value written in the memory 6b as a calculation result of the signal level of the first interference signal of one scan position is a significant value or not, that is, whether reflected light of the light of wavelength λ1 has been detected or not.

Then, when the determination section 6c determines that the value written in the memory 6b as a calculation result of the signal level of the first interference signal of one scan position is a significant value, the determination section 6c judges that object light entering the radiation/reception unit 2 has such intensity that the object light can be detected. The determination section 6c then outputs a calculation continuing instruction, which is an instruction for the continuation of calculation and the like concerning the current scan position, to the computing section 6a.

When the determination section 6c determines that the value written in the memory 6b as a calculation result of the signal level of the first interference signal is not a significant value, the determination section 6c judges that object light entering the radiation/reception unit 2 has such intensity that the object light cannot be virtually detected. The determination section 6c then outputs an instruction of changing the scan position from the current scan position to another scan position to the computing section 6a.

Next, operations of the biological observation apparatus 1B according to the second embodiment will now be described with reference to a flowchart shown in FIG. 17.

After each part of the biological observation apparatus 1B is powered up, the switches, which are mounted in the operation device (not shown) are turned on. Thereby, the apparatus 1B is instructed to start obtaining biological information of the living tissue 101.

The driving signal generator 4 outputs an ultrasound wave drive signal for radiating a predetermined ultrasound wave to the ultrasound transducer 26 via the amplifier 5 in response to the instruction.

In step S21, the ultrasound transducer 26 and the acoustic lens 26a radiate a predetermined ultrasound wave, in response to the ultrasound wave drive signal received from the amplifier 5, in the direction in which light is radiated and toward the living tissue 101.

Meanwhile, the driving signal generator 4 generates a light source drive signal for making the unit 2 emit light having a wavelength of λ1 in response to the instruction, and outputs the light source drive signal to the light source 21.

In step S22, the light source 21 radiates light having a wavelength of λ1 to the half mirror 22 at one scan position in response to the light source drive signal received from the driving signal generator 4.

Thereafter, as in the case of the first embodiment, object light, which is the light reflected at the position (position of $Z=Z_0$) corresponding to the area at which the ultrasound wave converges, enters the half mirror 22.

The object light entering the half mirror 22 from the ultrasound transducer 26 and the acoustic lens 26a interferes with the reference light coming from the reference mirror 25 and enters the light detector 27 as first interference light.

In step S23, the light detector 27 applies heterodyne detection to the first interference light coming from the half mirror 22, and converts the detected first interference light into a first interference signal, which is an electric signal. The light detector 27 outputs the first interference signal to the signal processor 6A.

In step S24, the computing section 6a of the signal processor 6A calculates the signal level of the first interference signal as $I(\lambda 1, Z_0)$ which is shown by the expression (2), based on the first interference signal. The computing section 6a then writes the calculated value into the memory 6b.

In step S25, the determination section 6c determines whether or not a value written in the memory 6b as a calculation result of the signal level of the first interference signal for one area of one scan position is a significant value, that is, a non-zero value.

Then, when the determination section 6c determines that the value written in the memory 6b as a calculation result of the signal level of the first interference signal for one area of one scan position is a significant value, the determination section 6c judges that object light entering the radiation/reception unit 2 has such intensity that the object light can be detected. The determination section 6c outputs a calculation continuing instruction, which is an instruction for the continuation of calculation and the like for the one area of the one scan position, to the computing section 6a.

When the determination section 6c determines that the value written in the memory 6b as a calculation result of the signal level of the first interference signal is not a significant value, that is, a value of zero, the determination section 6c judges that object light entering the radiation/reception unit 2 has such intensity that the object light cannot be virtually detected. The determination section 6c then outputs an instruction of changing the scan position from the current scan position to another scan position to the computing section 6a. Then, when the computing section 6a receives the instruction from the determination section 6c, the computing section 6a subsequently performs a process (described later) shown in step S33.

Meanwhile, after the computing section 6a writes the calculation result of the signal level of the first interference signal into the memory 6b, when the computing section 6a receives the calculation continuing instruction from the determination section 6c, the computing section 6a outputs a control signal for changing the wavelength of light radiated to the living tissue 101 to the driving signal generator 4.

The driving signal generator 4 outputs an ultrasound wave drive signal for radiating a predetermined ultrasound wave to the ultrasound transducer 26 via the amplifier 5 at the timing when the control signal is inputted from the signal processor 6A. The driving signal generator 4 then outputs a light source drive signal for changing the wavelength of light radiated to the living tissue 101 from λ1 to λ2.

In step S26, the ultrasound transducer 26 and the acoustic lens 26a radiate a predetermined ultrasound wave, in response to the ultrasound wave drive signal received from the amplifier 5, in the direction in which light is radiated and toward the living tissue 101. In step S27, the light source 21 radiates the light of wavelength λ2 to the half mirror 22 in response to the light source drive signal received from the driving signal generator 4.

The light of wavelength λ2 is reflected from the position of $Z=Z_0$ as in the case of the light of wavelength λ1. The reflected light passes through the opening of the ultrasound transducer 26 and the acoustic lens 26a and enters the half mirror 22 as object light.

The object light coming from the ultrasound transducer 26 and the acoustic lens 26a interferes with the reference light coming from the reference mirror 25 in the half mirror 22 and enters the light detector 27 as second interference light.

In step S28, the light detector 27 applies heterodyne detection to the second interference light coming from the half mirror 22, and converts the detected second interference light into a second interference signal, which is an electric signal. The light detector 27 outputs the second interference signal to the signal processor 6A.

In step S29, the computing section 6a of the signal processor 6A calculates the signal level of the second interference signal, which is shown as $I(\lambda 2, Z_0)$ by the expression (4), based on the second interference signal. In step S30, the computing section 6a calculates the difference value $\Delta I$ between the signal level of the first interference signal shown by the expression (5) and the signal level of the second interference signal shown by the expression (6) by using the expression (7).

Then, in step S31, the computing section 6a applies FFT (fast Fourier transformation) to the right side of the expression (7), thereby, calculating a variation of the Doppler shift amount $\Delta f_{ds}$ at one area of one scan position as shown in the expression (8). In addition, the computing section 6a obtains a calculation result of the expression (11) by using the expressions (8), (9) and (10).

In step S32, the computing section 6a assumes the value of the right side of the expression (11), which is a value obtained by subtracting the amount of change in the index of refraction of tumor tissue generated when the light of wavelength $\lambda 2$ is emitted from the amount of change in the index of refraction of the rumor tissue generated when the light of wavelength $\lambda 1$ is emitted, as a pixel value of the one area of the current scan position and produces image data of is the one area of the current scan position. Then, the computing section 6a relates the produced image data to scan positional information, which shows positions within a scan range where the scan can be performed by the scan unit 3, and positional information in the Z-axis direction, and stores the image data, the scan positional information, and the positional information in the Z-axis direction in the memory 6b.

The operations of the steps S21 to S32 are performed multiple times while changing the position, at which the ultrasound wave converges, in the depth direction (Z-axis direction shown in FIG. 1) of the living tissue 101 (that is, $z=Z_0, Z1, Z2, \ldots$) by the acoustic lens 26a under the control of the signal processor 6.

In step S33, the computing section 6a determines whether or not the current scan position at which the image data is obtained is the end position of the scan range of the scan unit 3. When the current scan position at which the image data is obtained is not the end position of the scan range of the scan unit 3 (that is, when the whole scan is not completed), in step S34, the computing section 6a controls the scan signal generator 9 to change the scan position from the current scan position to another scan position (in the X-axis or Y-axis direction shown in FIG. 16). In addition, the computing section 6a outputs a control signal to the driving signal generator 4 to change the wavelength of light radiated to the living tissue 101. Thereafter, each part of the biological observation apparatus 1B repeats the above described operations until the computing section 6a determines, in step S33, that the current scan position is the end position of the scan range of the scan unit 3.

Note that, after the process in step S25, when the computing section 6a subsequently performs the processes in steps S33 and S34, the computing section 6a does not output the control signal for changing the wavelength of light radiated to the living tissue 101 to the driving signal generator 4 in order to make the light source 21 radiate the light of wavelength $\lambda 1$ again.

Thereafter, when the computing section 6a detects a state in which the scan is completed based on a trigger signal outputted from the driving signal generator 4, in step S35, the computing section 6a performs mapping to produce image data for one frame. The mapping is performed by using the image data, and the scan positional information and the positional information in the Z-axis direction related to the image data, which are stored in the memory 6b between the time when the previous trigger signal is inputted and the time when the current trigger signal is inputted. The computing section 6a converts the image data for one frame into a video signal and outputs the video signal to the display unit 8. Thereby, based on the image data, the display unit 8 displays an image (tomographic image) inside the living tissue 101 in a plane such as an X-Z plane shown in FIG. 16.

The biological observation apparatus 1B of the second embodiment shown in FIG. 16 having the configuration described above provides the same advantages as those of the biological observation apparatus 1 of the first embodiment.

Note that, in the biological observation apparatus 1B of the second embodiment, for example, when it is determined at least a predetermined number of times that the value written in the memory 6b is not significant, the biological observation apparatus 1B may skip the process for producing image data for one frame (the process in step S35 shown in FIG. 12) to prevent the image which is not suitable for observation from being produced. In addition, while skipping the process for producing image data for one frame (the process in step S35 shown in FIG. 12), a notification that the image suitable for observation cannot be obtained may be provided on the display unit 8.

The biological observation apparatus 1B shown in FIG. 16 may be modified to a configuration which provides the same advantages described above. The biological observation apparatus 1B may be modified to emit the light of wavelength $\lambda 1$ and the light of wavelength $\lambda 2$ from two separate light sources, respectively. In addition, in the biological observation apparatus 18 shown in FIG. 16, a light absorber composed of a board having a black color or the like may be disposed instead of the reference mirror 25 as in the case of FIG. 8. In addition, the biological observation apparatus 1B shown in FIG. 16 may be modified to a configuration in which the light of wavelength $\lambda 1$ and the light of wavelength $\lambda 2$ are emitted from two separate light sources, respectively, and a light absorber composed of a board having a black color or the like is disposed instead of the reference mirror 25 as in the case of FIG. 9.

According to the biological observation apparatus and method of the embodiments of the present invention, the burden on an operator can be reduced when treating tumor tissue.

Although the description above contains many specificities, these should not be construed as limiting the scope of the invention but as merely providing illustrations of some of the presently preferred embodiments of the present invention. Thus the scope of the present invention should be determined by the appended claims.

What is claimed is:

1. A biological observation apparatus comprising:
 a sound wave radiating unit configured to radiate a sound wave into an object to be examined;

a light radiating unit configured to radiate a first light having a first wavelength and a second light having a second wavelength into a portion of the object influenced by the sound wave;

a detector configured to detect reflected light of the first light and reflected light of the second light; and a calculator configured to calculate characteristic information of the object based on the reflected light of the first light and the reflected light of the second light, wherein a first absorption characteristic of the first light and a second absorption characteristic of the second light have sensitivities that are lower with respect to a change of oxygen saturation in blood of the object, and the first absorption characteristic and the second absorption characteristic are substantially equal to each other with respect to blood having different oxygen saturations, and the calculator configured to calculate a difference value between intensity of the reflected light of the first light and an intensity of reflected light of the second light and to produce image data of the object based on the difference value, and wherein the calculator is configured to apply a frequency analysis to the difference value, thereby calculating a variation of an amount of frequency modulation at the portion of the object influenced by the sound wave, and to produce the image data of the object based on the amount of frequency modulation.

2. The apparatus according to claim 1, further comprising a determination unit configured to determine whether or not the detector has detected the reflected light of the first light, wherein the light radiating unit radiates the second light when the determination unit determines that the detector has detected the reflected light of the first light.

3. The apparatus according to claim 1, further comprising a display configured to display a tomographic image of the object based on the image data.

4. The apparatus according to claim 1, wherein the light radiating unit is configured to radiate the first wavelength of the first light and the second wavelength of the second light within a range from 800 nm to 930 nm.

5. The apparatus according to claim 1, wherein the light radiating unit includes a first light radiating unit that radiates the first light and a second light radiating unit that radiates the second light.

6. The apparatus according to claim 1, wherein an angle of a direction in which the first light and the second light are radiated and an angle of a direction in which the sound wave is radiated are different from each other with respect to the object.

7. The apparatus according to claim 1, wherein the first wavelength of the first light and the second wavelength of the second light are 130 nm apart.

8. The apparatus according to claim 1, wherein the absolute value of the difference between the first wavelength and the second wavelength is at least substantially 100 nm.

9. A biological observation method comprising the steps of:

radiating a sound wave into an object to be examined;

radiating a first light having a first wavelength into a portion of the object influenced by the sound wave;

detecting reflected light of the first light;

radiating a second light having a second wavelength into the portion of the object influenced by the sound wave;

detecting reflected light of the second light; and calculating characteristic information of the object based on the reflected light of the first light and the reflected light of the second light, wherein a first absorption characteristic of the first light and a second absorption characteristic of the second light have sensitivities that are lower with respect to a change of oxygen saturation in blood of the object, and the first absorption characteristic and the second absorption characteristic are substantially equal to each other with respect to blood having different oxygen saturation, and in the step of calculating characteristic information of the object, a difference value between an intensity of the reflected light of the first light and intensity of the reflected light of the second light is calculated, and image data of the object is produced based on the difference value, wherein, in the step of calculating characteristic information of the object, a frequency analysis is applied to the difference value, thereby calculating a variation of an amount of frequency modulation at the portion of the object influenced by the sound wave, and the image data of the object is produced based on the amount of frequency modulation.

10. The method according to claim 9, further comprising:
determining whether or not the reflected light of the first light has been detected, and
radiating the second light when it is determined that the reflected light of the first light has been detected.

11. The method according to claim 9, further comprising:
displaying a tomographic image of the object based on the image data.

12. The method according to claim 9, wherein the first wavelength of the first light and the second wavelength of the second light are selected within a range from 800 nm to 930 nm.

13. The method according to claim 9, wherein the first wavelength of the first light and the second wavelength of the second light are 130 nm apart.

14. The method according to claim 9, wherein the absolute value of the difference between the first wavelength and the second wavelength is at least substantially 100 nm.

* * * * *